United States Patent
Tojo et al.

(10) Patent No.: US 10,451,409 B2
(45) Date of Patent: Oct. 22, 2019

(54) INSERTION SYSTEM

(71) Applicant: OLYMPUS CORPORATION, Tokyo (JP)

(72) Inventors: Ryo Tojo, Hachioji (JP); Hiromasa Fujita, Hachioji (JP)

(73) Assignee: Olympus Corporation, Tokyo (JP)

(*) Notice: Subject to any disclaimer, the term of this patent is extended or adjusted under 35 U.S.C. 154(b) by 0 days.

(21) Appl. No.: 16/009,442

(22) Filed: Jun. 15, 2018

(65) Prior Publication Data

US 2018/0292199 A1    Oct. 11, 2018

Related U.S. Application Data

(63) Continuation of application No. PCT/JP2015/085547, filed on Dec. 18, 2015.

(51) Int. Cl.

| | |
|---|---|
| *G01B 11/24* | (2006.01) |
| *A61B 5/06* | (2006.01) |
| *A61B 1/005* | (2006.01) |
| *A61B 1/05* | (2006.01) |
| *A61B 34/20* | (2016.01) |

(Continued)

(52) U.S. Cl.
CPC ............. *G01B 11/24* (2013.01); *A61B 1/005* (2013.01); *A61B 1/0051* (2013.01); *A61B 1/05* (2013.01);
(Continued)

(58) Field of Classification Search
CPC ......... A61B 34/20; A61B 1/0051; A61B 1/05; A61B 1/005; A61B 5/067;
(Continued)

(56) References Cited

U.S. PATENT DOCUMENTS

| | | | | |
|---|---|---|---|---|
| 4,930,494 A | * | 6/1990 | Takehana ........... | A61B 1/00147 600/145 |
| 2002/0183592 A1 | * | 12/2002 | Suzuki ............... | A61B 1/00071 600/145 |

(Continued)

FOREIGN PATENT DOCUMENTS

| | | |
|---|---|---|
| JP | H11-19027 A | 1/1999 |
| JP | 2003-052614 A | 2/2003 |

(Continued)

OTHER PUBLICATIONS

International Search Report dated Mar. 15, 2016 issued in PCT/JP2015/085547.

(Continued)

*Primary Examiner* — Sang H Nguyen
(74) *Attorney, Agent, or Firm* — Scully Scott Murphy & Presser, P.C.

(57) ABSTRACT

An insertion system includes an insertion apparatus including an insertion section, a fiber sensor configured to detect a bend shape of the insertion section, an attitude detector, and an attitude shape calculator. The attitude detector is configured to detect at least one of a first rotational change quantity related to a change quantity of rotation about a longitudinal direction of the insertion apparatus, and a first directional change quantity related to a change quantity of the longitudinal direction. The attitude shape calculator is configured to calculate attitude shape information including at least one of a change quantity of rotation of the bend shape and a change quantity of a direction of the bend shape, based on the bend shape and the at least one of the first rotational change quantity and first directional change quantity.

34 Claims, 18 Drawing Sheets

(51) Int. Cl.
*A61M 25/01* (2006.01)
*G01V 7/06* (2006.01)
*G02B 23/24* (2006.01)
*G01V 8/16* (2006.01)
*G02B 6/02* (2006.01)

(52) U.S. Cl.
CPC .............. *A61B 5/067* (2013.01); *A61B 34/20* (2016.02); *A61M 25/0105* (2013.01); *G01V 7/06* (2013.01); *G01V 8/16* (2013.01); *G02B 23/2469* (2013.01); *A61B 2034/2061* (2016.02); *A61B 2562/0219* (2013.01); *A61M 2025/0166* (2013.01); *G02B 6/02052* (2013.01)

(58) Field of Classification Search
CPC ...... A61B 2019/2211; A61B 2019/466; A61B 2019/467; A61B 2019/502; A61B 2019/5255; A61B 2019/5261; A61B 25/0105; G01B 2019/464; G01B 11/24; G01V 7/06; G01V 8/16
See application file for complete search history.

(56) References Cited

U.S. PATENT DOCUMENTS

| | | |
|---|---|---|
| 2006/0074289 A1 | 4/2006 | Adler et al. |
| 2010/0160728 A1* | 6/2010 | Yoshie ............... A61B 1/00147 600/109 |
| 2012/0143203 A1* | 6/2012 | Nishio ............... A61B 17/1631 606/96 |
| 2013/0201311 A1 | 8/2013 | Hirakawa |
| 2015/0208947 A1* | 7/2015 | Tojo ................... G02B 23/2476 600/104 |
| 2015/0223670 A1* | 8/2015 | Fujita ................. A61B 1/00036 600/109 |
| 2015/0359419 A1 | 12/2015 | Hane et al. |
| 2016/0128552 A1* | 5/2016 | Tojo ................... A61B 1/00057 600/102 |

FOREIGN PATENT DOCUMENTS

| | | |
|---|---|---|
| JP | 2006-81900 A | 3/2006 |
| JP | 2014-161374 A | 9/2014 |
| WO | 2013/018404 A1 | 2/2013 |

OTHER PUBLICATIONS

Japanese Office Action dated Mar. 12, 2019 in Japanese Patent Application No. 2017-556303.
International Preliminary Report and Written Opinion dated Jun. 28, 2018 received in PCT/JP2015/085547.

* cited by examiner

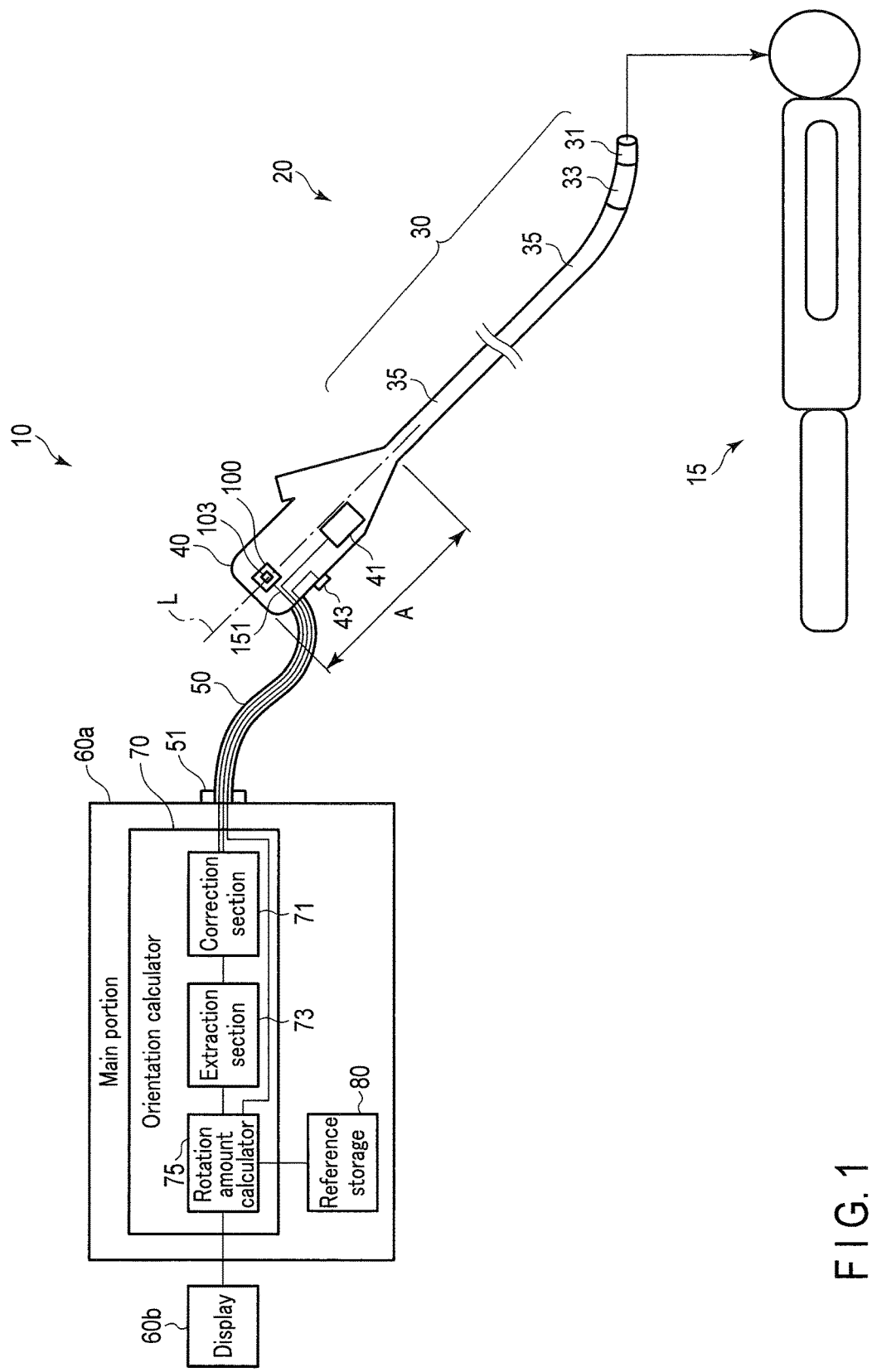
F I G. 1

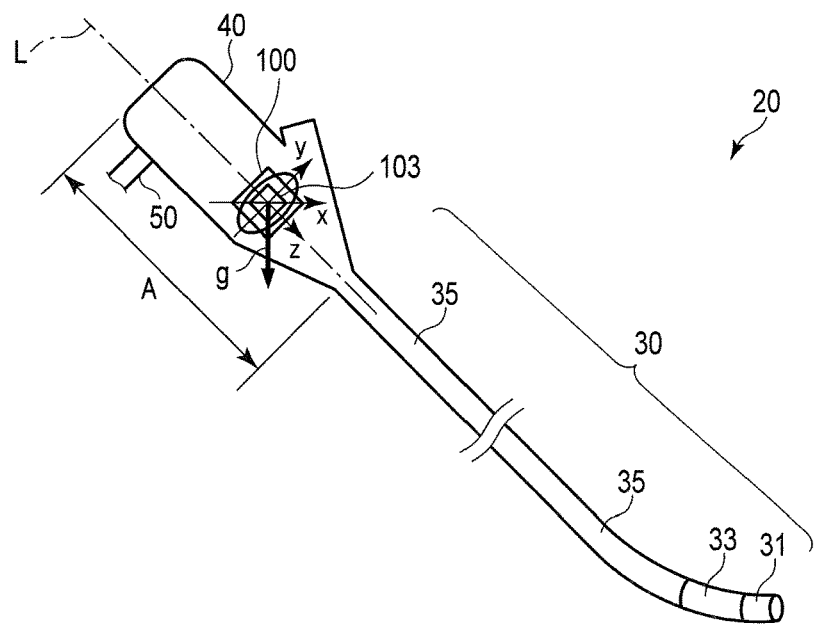
F I G. 2A
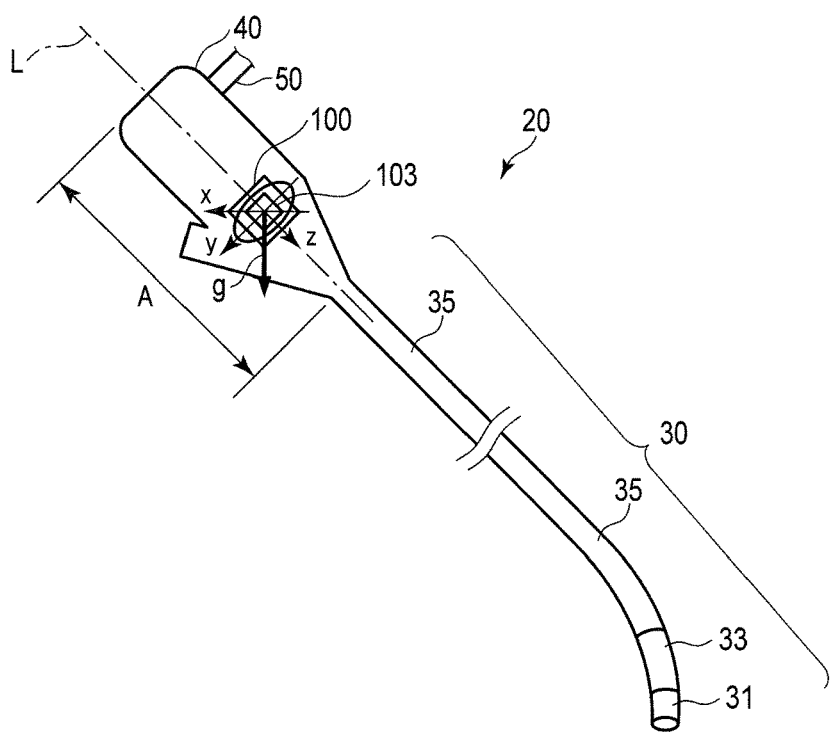
F I G. 2B

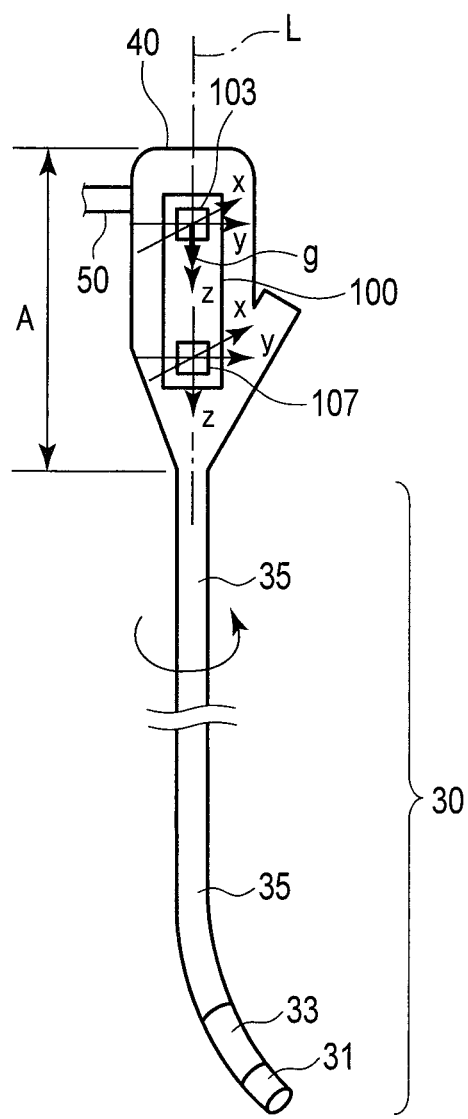
F I G. 7

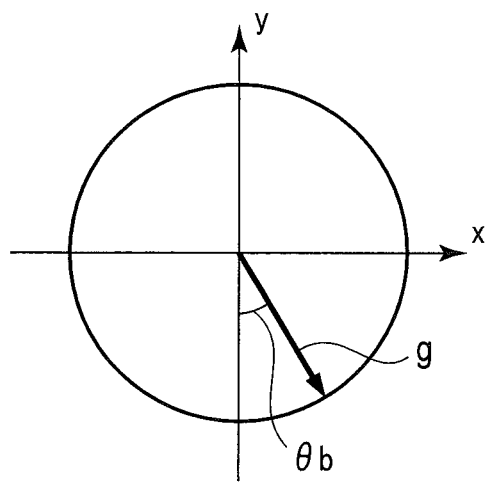
F I G. 10C
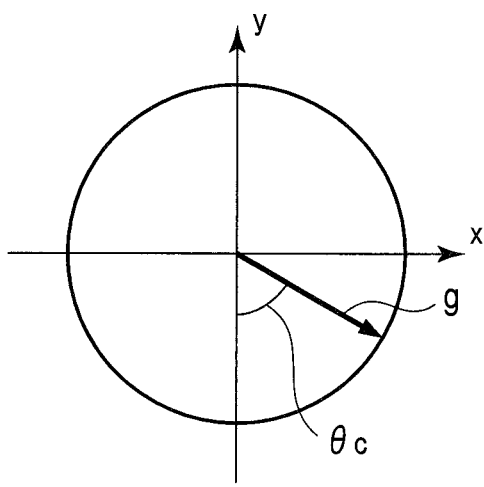
F I G. 10D $\theta t = 60°$

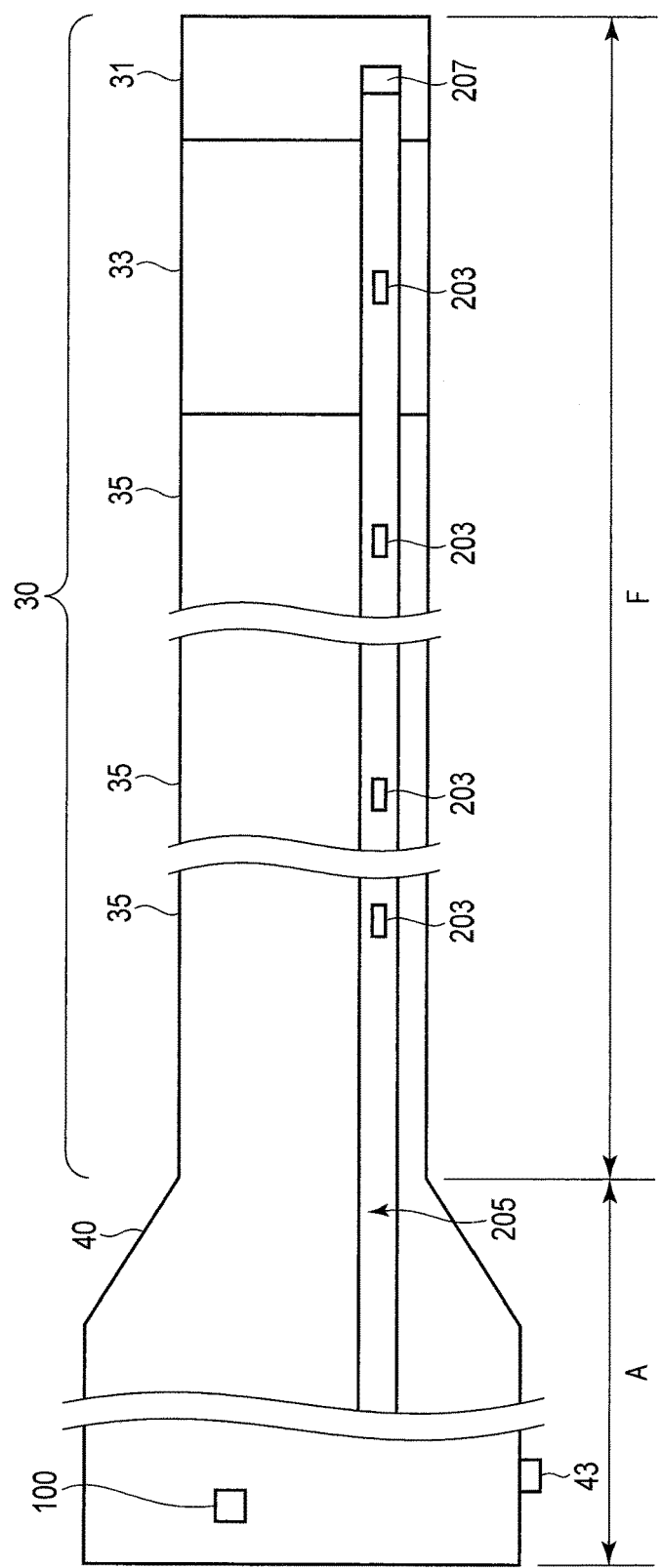
F I G. 13C

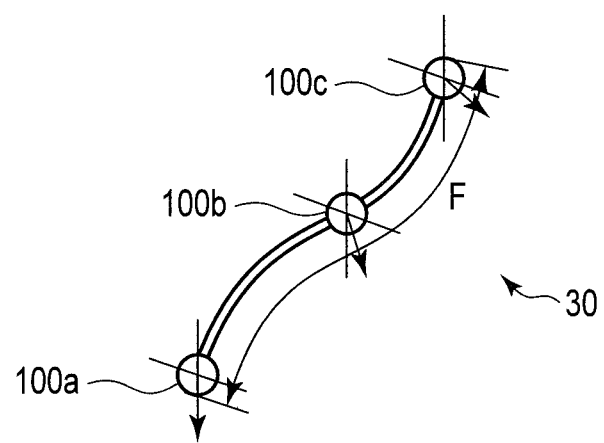
F I G. 15

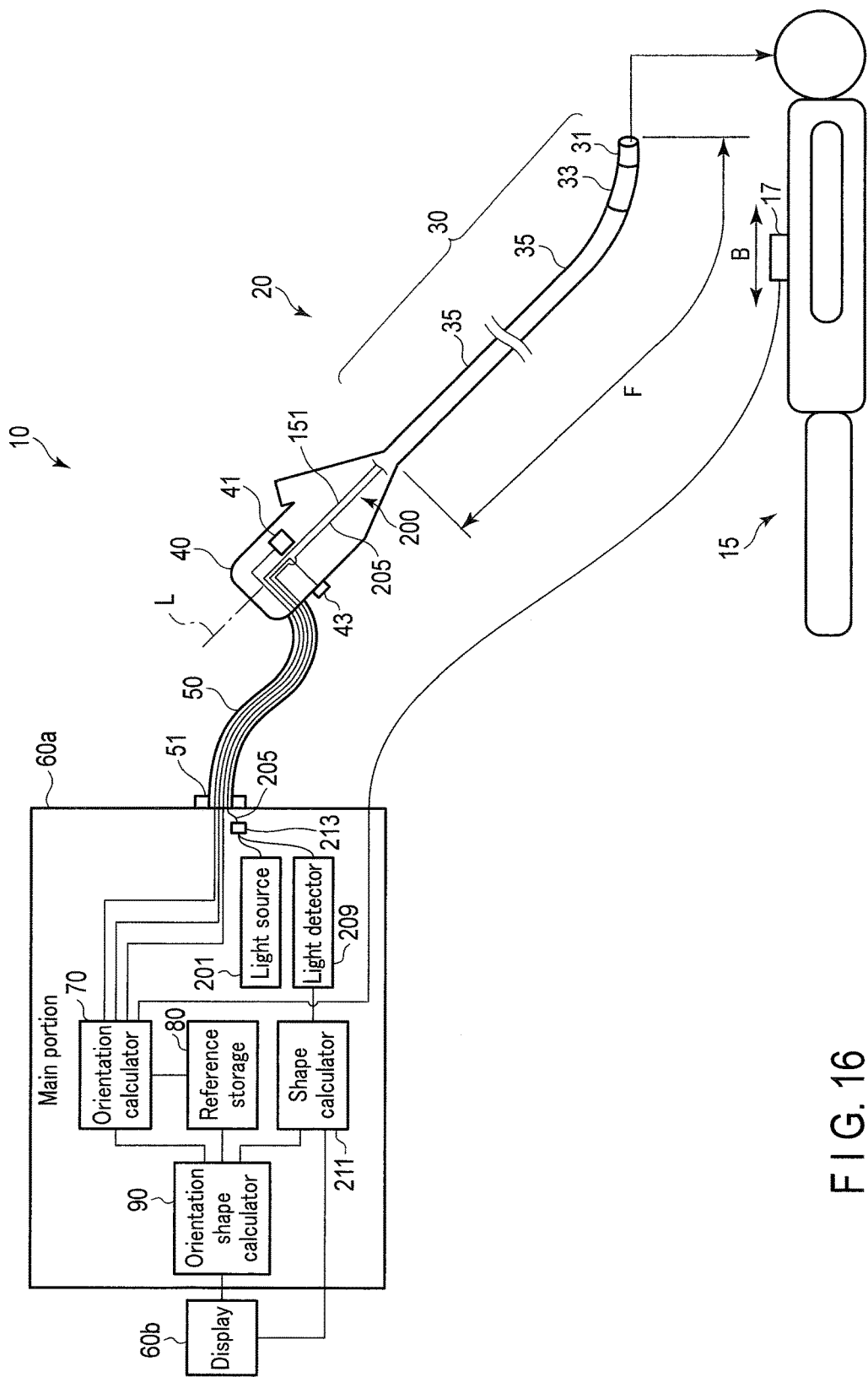
F I G. 16

INSERTION SYSTEM

CROSS-REFERENCE TO RELATED APPLICATIONS

This application is a Continuation Application of PCT Application No. PCT/JP2015/085547, filed Dec. 18, 2015, the entire contents of all of which are incorporated herein by reference.

BACKGROUND OF THE INVENTION

1. Field of the Invention

The present invention relates to an insertion system.

2. Description of the Related Art

For example, Jpn. Pat. Appln. KOKAI Publication No. 2003-52614 discloses a flexible endoscope apparatus comprising a flexible tube and flexible bend detection optical fibers. Each bend detection optical fiber comprises a bend detector for detecting the light transmission quantity of light that changes in accordance with the bend angle of the bend detection optical fiber. The bend detection optical fibers are attached to a flexible belt-like member provided on the flexible tube to be parallel with one another, and are arranged inside the flexible tube over almost the entire length of the flexible tube. The bend shape of the belt-like member at a portion where each bend detector is located is detected based on the light transmission quantity of each bend detection optical fiber. The bend shape of the belt-like member is displayed on a display screen of a display as the bend shape of the flexible tube. The flexible endoscope apparatus functions as a fiber sensor that detects the bend shape (bend direction and bend magnitude) of the bent insertion apparatus.

BRIEF SUMMARY OF THE INVENTION

An insertion system includes an insertion apparatus including an insertion section to be inserted into a subject, a fiber sensor arranged in the insertion section and configured to detect a bend shape of a desired shape detection range of the insertion section, at least one attitude detector arranged in the insertion apparatus and configured to detect at least one of a first rotational change quantity related to a change quantity of rotation about an axis in a longitudinal direction of the insertion apparatus at an arrangement position, and a first directional change quantity related to a change quantity of the longitudinal direction of the insertion apparatus at the arrangement position, and an attitude shape calculator configured to calculate attitude shape information including at least one of a change quantity of rotation of the bend shape and a change quantity of a direction of the bend shape, based on the bend shape detected by the fiber sensor and the at least one of the first rotational change quantity and first directional change quantity detected by the attitude detector.

Advantages of the invention will be set forth in the description that follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute apart of the specification, illustrate embodiments of the invention, and together with the general description given above and the detailed description of the embodiments given below, serve to explain the principles of the invention.

FIG. 1 is a schematic diagram of an insertion system including a gravity sensor according to a first embodiment of the present invention.

FIG. 2A is a diagram illustrating the coordinate system of an acceleration sensor in the gravity sensor.

FIG. 2B is a diagram of the insertion apparatus rotated 180 degrees about the axis in the longitudinal direction of the control section from the state of FIG. 2A.

FIG. 7 is a schematic diagram of an insertion apparatus including an acceleration sensor and a gyro sensor.

FIG. 10C is a diagram illustrating second rotational change quantity $\theta b$.

FIG. 10D is a diagram illustrating second rotational change quantity $\theta c$.

FIG. 13C is a diagram illustrating an example of the positional relationship between the attitude detector and detection targets in the shape detection range.

FIG. 15 is a diagram showing a second modification of the second embodiment, and illustrating calculation of attitude shape information based on the quantity of twist in the shape detection range.

FIG. 16 is a schematic diagram of the insertion system according to a third modification of the second embodiment.

DETAILED DESCRIPTION OF THE INVENTION

Figure 3A:
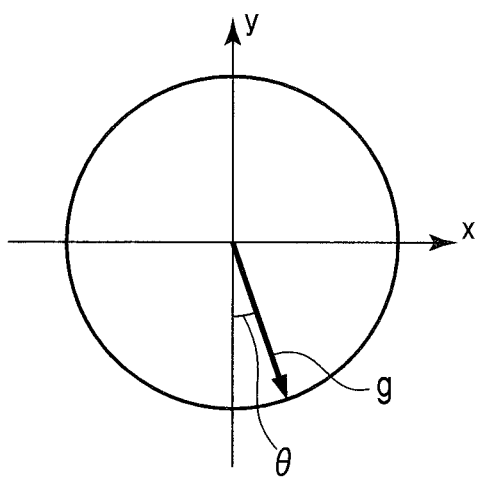
FIG. 3A is a diagram illustrating the second rotational change quantity.

Hereinafter, embodiments of the present invention will be described in detail with reference to the drawings. In some drawings, the members are partly omitted for clarification of illustration.

First Embodiment

Hereinafter, a first embodiment will be described.

As shown in FIG. 1, the insertion system 10 includes an insertion apparatus 20, a main body 60a, and a display 60b.

The insertion apparatus 20 of the present embodiment is described as, but is not limited to, a flexible endoscope for medical use, for example. The insertion apparatus 20 may be, for example, a rigid endoscope for medical use, a flexible endoscope for industrial use, a rigid endoscope for industrial use, a catheter, or a treatment tool. The insertion apparatus 20 has only to include an insertion section 30 to be inserted into a subject 15. The insertion section 30 of the present embodiment may be flexible or rigid. The subject 15 is not limited to a person, and may be an animal, or another structure, for example.

The insertion apparatus 20 includes an insertion section 30 to be inserted into the subject 15, an control section 40 connected to a proximal end of the insertion section 30 to operate the insertion apparatus 20, and a cord 50 connected to the control section 40. The cord 50 includes a connector 51 arranged at an end of the cord 50 and detachably attached to the main body 60a.

The insertion section 30 is, for example, hollow and elongated. The insertion section 30 includes a hard distal end 31, a bendable portion 33, and a flexible tube 35 in this order from the distal end of the insertion section 30 toward the proximal end of the insertion section 30. Various internal members corresponding to the use of the insertion apparatus 20 are arranged inside the hard distal end 31. The internal members include, for example, an imaging device 31a (see FIG. 12) and an object lens (not shown) optically connected to the imaging device 31a. The imaging device 31a includes, for example, a CCD. The internal members further include an illumination section (not shown) that illuminates the inside of the subject 15 by using source light emitted from a light source unit (not shown and to be described later) provided in the main body 60a as illumination light, and an opening (not shown) of a channel (not shown) through which a treatment tool (not shown) separate from the insertion apparatus 20 is inserted. When the imaging device 31a images the inside of the subject 15, the imaging device 31a transmits an image signal to an image processor (not shown and to be described later) of the main body 60a. The bendable portion 33 is connected to a bend control section (not shown) provided in the control section 40 through an operation wire (not shown) provided inside the insertion section 30. The bendable portion 33 is configured to be actively bent by a desired quantity in a desired direction by the operation wire being pulled by the operation of the bend control section. When the bendable portion 33 receives an external force, the bendable portion 33 is configured to be passively bent by the external force. The flexible tube 35 is flexible, and configured to be passively bent by an external force. The flexible tube 35 is longer than each of the hard distal end 31 and the bendable portion 33. The distal end of the flexible tube 35 may include the hard distal end 31 and the bendable portion 33, and functions as the distal end of the insertion section 30.

The control section 40 is held by one hand of the operator.

The operator inserts the insertion section 30 into the subject 15 from an opening of the subject 15 (such as the mouth of the patient). Then, the operator observes and treats the inside of the subject 15.

The main body 60a includes therein a light source unit (not shown) and an image processor (not shown).

The light source unit includes a light source (not shown) that emits source light. The light source includes at least one of a lamp, such as a xenon lamp or a halogen lamp, and a semiconductor light source, such as an LED or an LD. The source light emitted from the light source is guided to the illumination section by a light guiding member (not shown) built in the cord 50, the control section 40, and the insertion section 30. The optical characteristics of the source light are desirably converted by the illumination section, whereby the source light is converted into illumination light. The illumination light is emitted from the illumination section, and illuminates the inside of the subject 15.

The image processor transmits an image signal of the inside of the subject 15 produced by the imaging device 31a through a signal line (not shown) built in the insertion section 30, the control section 40, and the cord 50. The image processor processes the image signal, and the display 60b displays the image.

The main body 60a further includes therein an attitude calculator 70 constituted by a calculation circuit or the like including, for example, a CPU or an ASIC, and a reference storage 80, such as a memory. As will be described in detail later, the attitude calculator 70 is to calculate attitude information of the insertion apparatus 20. The attitude information includes, for example, information on the current attitude of the insertion apparatus 20 and information on the change in the attitude. The attitude of the insertion apparatus 20 includes, for example, the attitude of the attitude detection area to be described later. The attitude calculator 70 converts attitude information of the insertion apparatus 20 into, for example, a numerical value to be described later, which is a form displayed by the display 60b. The reference storage 80 will be described later.

The display 60b is a general display device, such as a liquid crystal display, a CRT display, or an organic EL display. The display 60b displays an image of the inside of the subject 15 produced by the imaging device 31a. The display 60b displays attitude information of the insertion apparatus 20 as, for example, a numerical value, a graph, or an image. This image may be 2D or 3D. The display 60b may display a figure of the insertion apparatus 20. The display 60b may change the figure of the displayed insertion apparatus 20 in accordance with attitude information calculated by the attitude calculator 70. In place of the display 60b, an output device that outputs sound or the like may be provided. That is, the insertion system 10 may include any notifying device that notifies the operator of attitude information in some form.

The insertion apparatus 20 includes therein at least one attitude detector 100. In the present embodiment, one attitude detector 100 is provided. The attitude detector 100 has an attitude detection area (hereinafter referred to as area A) desirably defined. Area A is an area around the attitude detector 100 including the attitude detector 100, and is not separated from the attitude detector 100. For example, the attitude detector 100 may be located at the center of area A. Area A refers to an area of which attitude information can be detected by the attitude detector 100. The attitude detector 100 is configured to detect at least one of a first rotational change quantity that is a change quantity of area A about the axis in the longitudinal direction of area A, and a first directional change quantity that is a change quantity of area A in the longitudinal direction of area A. The longitudinal direction of area A is arranged along the longitudinal direction L of the control section 40. The longitudinal direction L of the control section 40 corresponds to the longitudinal direction of the insertion section 30 and the longitudinal direction of the insertion apparatus 20. The first rotational change quantity and the first directional change quantity are attitude information of area A. The attitude detector 100 is electrically connected to the attitude calculator 70 through a signal line 151. The attitude detector 100 may be electrically connected to the attitude calculator 70 wirelessly. For example, the attitude detector 100 always outputs the detection result in real time to the attitude calculator 70. Then, the attitude calculator 70 calculates attitude information of the insertion apparatus 20 based on at least one of the first rotational change quantity and first directional change quantity detected by the attitude detector 100.

In the present embodiment, the attitude detector 100 is built in the control section 40 that is a rigid portion. Part of the control section 40 is not changed relative to the other part of the control section 40, i.e., is not bent or flexed relative to the other part. Therefore, the entire rigid portion like the control section 40 can be defined as area A; and the first rotational change quantity of area A can be regarded as the first rotational change quantity of the control section 40, and the first directional change quantity of area A as the first directional change quantity of the control section 40. Accordingly, the attitude detector 100 is configured to detect at least one of the first rotational change quantity and first directional change quantity of the control section 40. The first rotational change quantity and first directional change quantity of the control section 40 are included in attitude information of the control section 40.

When the attitude detector 100 is built in the control section 40, since the control section 40 is a rigid portion, a change in the attitude of part of the control section 40 can be regarded as a change in the attitude of the entire control section 40. In this state, the entire control section 40 can be set as area A.

In, for example, a flexible endoscope, it is assumed that the attitude detector 100 is built in the control section 40, the entire insertion section 30 follows rotation of the control section 40 about the axis in the longitudinal direction L of the control section 40, and the rotation quantity of the distal end of the insertion section 30 can be regarded as always approximately equal to the rotation quantity of the proximal end of the insertion section 30 or the rotation quantity of the control section 40. In this case, it is possible to regard the entire range following rotation of the control section 40, such as the entire insertion section 30, as being included in area A. Therefore, the first rotational change quantity of the control section 40 detected by the attitude detector 100 can be regarded as the first rotational change quantity of the insertion section 30, and can be regarded as the first rotational change quantity of the insertion apparatus 20 itself.

Note that the portion in which the attitude detector 100 is built varies depending on the portion of which attitude is to be detected.

Figure 8A:
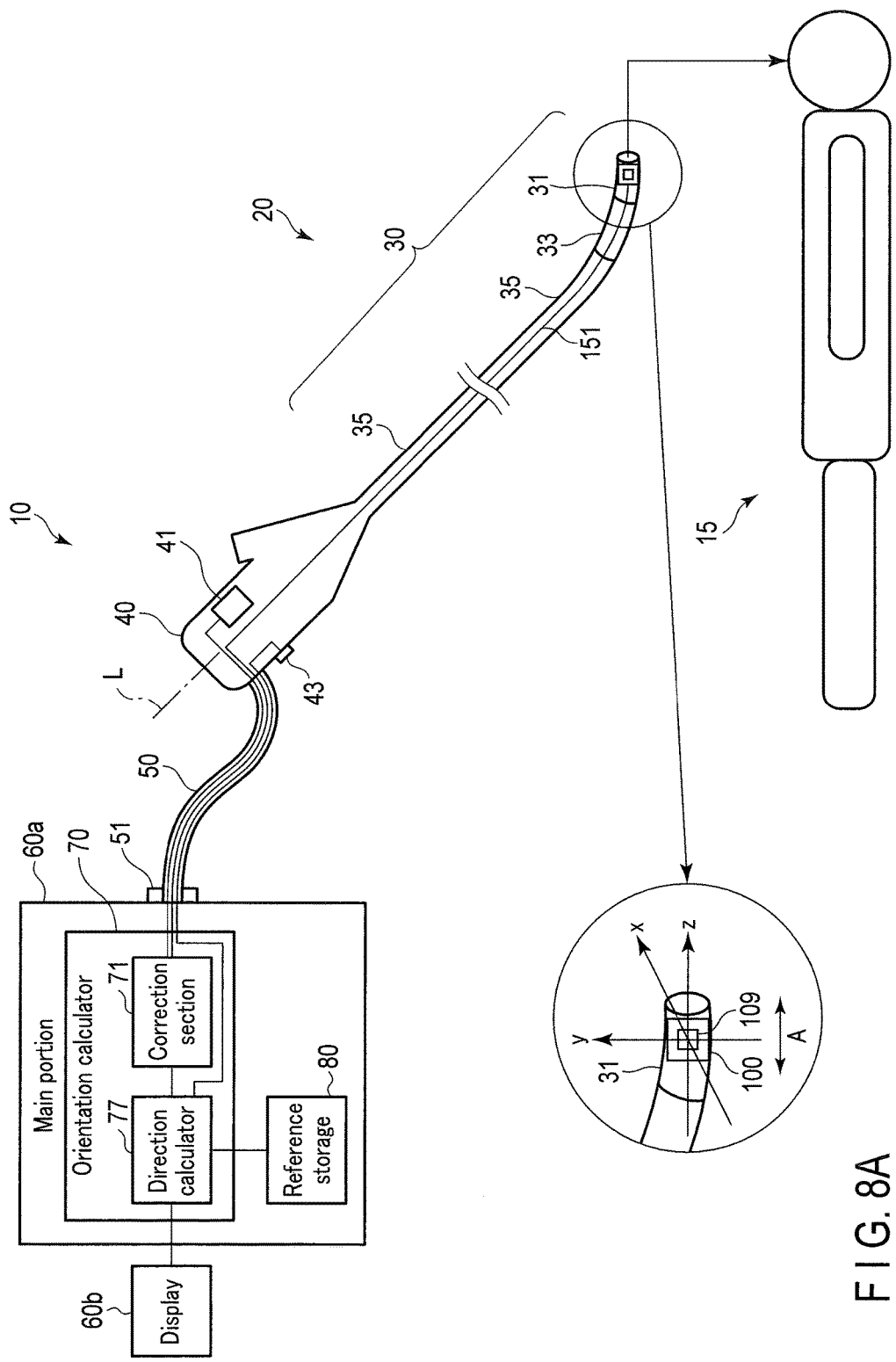
FIG. 8A is a schematic diagram of an insertion system including a terrestrial magnetism sensor.
Figure 9:
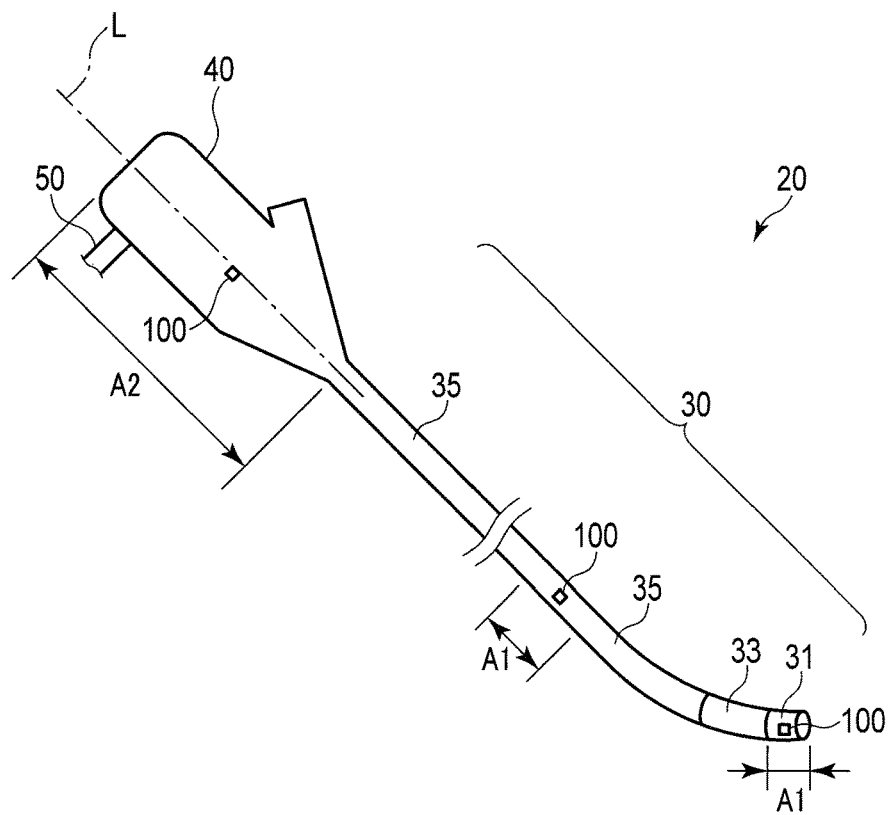
FIG. 9 is a diagram showing a first modification of the first embodiment, and illustrating arrangement positions of attitude detectors.

For example, when the attitude detector 100 needs to detect at least one of the first rotational change quantity and first directional change quantity of the distal end of the insertion section 30, the attitude detector 100 is built in the distal end (distal rigid portion 31) of the insertion section 30, as shown in FIGS. 8A and 9. The attitude detector 100 may be built in the vicinity of the distal end (such as the bendable portion 33) of the insertion section 30.

As shown in FIG. 9, the attitude detector 100 may be built in a flexible portion of the flexible endoscope. The flexible portion refers to, for example, the flexible tube 35. The flexible portion may be the bendable portion 33. Area A1 is, for example, an area of which attitude information can be detected by an attitude detector 100 built in the flexible portion. Area A2 is, for example, an area of which attitude information can be detected by an attitude detector 100 built in the rigid portion. Normally, if the positions in the longitudinal direction are different in the flexible portion, the attitudes are also different. Therefore, the range of area A1 is set smaller than the range of area A2. However, the length of area A1 may be adjusted as desired in accordance with the accuracy of attitude detection required for the use of the insertion apparatus 20. If a lower level of accuracy is acceptable, a wider range can be regarded as having the same attitude. Therefore, in the flexible portion, for example, a range of 5 cm in the longitudinal direction may be regarded as one attitude detection area. Even if the insertion section 30 is flexible, when the rotations of sections follow one another, the entire range in which the rotations follow one another may be one attitude detection area. The rotations following one another means that, for example, the rotation quantity of the proximal end of the insertion section 30 can always be regarded as almost the same as the rotation quantity of the distal end of the insertion section 30.

Furthermore, for example, if the insertion apparatus 20 is a rigid endoscope and the attitude detector 100 is built in somewhere in the rigid endoscope, the part in which the attitude detector 100 is arranged is not changed relative to the other part, i.e., is not bent or flexed relative to the other part. Therefore, the entire rigid portion, such as the entire rigid endoscope, can be defined as one area A. The attitude detector 100 is configured to detect at least one of the first rotational change quantity and first directional change quantity of the entire rigid endoscope.

The attitude detector 100 according to the present embodiment has, for example, one of the following configurations 1 to 5. The configuration of the main body 60a corresponds to the configuration of the attitude detector 100. Each configuration will be described below.

[Configuration 1 of Attitude Detector 100]

Hereinafter, Configuration 1 of the attitude detector 100 will be described with reference to FIGS. 1, 2A, 2B, 3A, 3B, and 4.

As shown in FIGS. 2A and 2B, the attitude detector 100 may include a gravity sensor configured to detect the direction g of gravity acting on area A and then detect the first rotational change quantity based on the detected direction g of gravity.

As shown in FIGS. 2A and 2B, the gravity sensor may include at least one acceleration sensor 103 configured to detect the direction g of gravity of two or more axes and then detect the first rotational change quantity based on the detected direction g of gravity. In the present embodiment, one acceleration sensor 103 is provided. Normally, the acceleration sensor 103 detects the acceleration of the counterforce to gravity. Since the direction of the counterforce is the opposite of gravity, the following descriptions will be provided while regarding the acceleration sensor 103 as capable of detecting the direction g of gravity. Furthermore, in the present embodiment, the acceleration sensor 103 detects gravity of three axes. FIG. 2B is a diagram of the insertion apparatus 20 rotated 180 degrees about the axis in the longitudinal direction L of the control section 40 from the state of FIG. 2A.

The type of the acceleration sensor 103 is not particularly limited as long as the acceleration sensor 103 can detect the direction g of gravity. Considering that the acceleration sensor 103 is built in the insertion apparatus 20 having a limited inner space, it is preferable that the acceleration sensor 103 be small. To serve the need, it is preferable that the acceleration sensor 103 be of a semiconductor piezoresistive type or a capacitance type using Micro Electro Mechanical Systems (hereinafter referred to as MEMS) technology.

As shown in FIGS. 2A and 2B, the coordinate system of the acceleration sensor 103 is defined as a right-handed system including an x axis, a y axis orthogonal to the x axis, and a z axis orthogonal to the x axis and the y axis. In this case, the acceleration sensor 103 is installed inside the control section 40 so that, in a state where the insertion section 30 is linearly arranged, the x axis and the y axis are arranged orthogonally to the longitudinal direction L of the control section 40, and the z axis is arranged along the longitudinal direction L of the control section 40, the y axis is arranged along the vertical axis of the image produced by the imaging device 31a, the positive direction of the y axis coincides with the positive direction of the vertical axis, and the x axis is arranged along the horizontal axis of the image. The positive direction of the y axis coinciding with the positive direction of the vertical axis means that the positive direction of the y axis coincides with the upward direction of the image displayed on the display 60b.

Although not shown, when the insertion apparatus 20 of the present embodiment is used, for example, a state where the z axis is arranged parallel to the ground is the reference of the first rotation change quantity of the control section 40 detected by the acceleration sensor 103. The parallel arrangement state indicates a state where the vertical axis of the imaging plane of the imaging device 31a having the vertical axis and the horizontal axis of the image is arranged perpendicular to the ground. The vertical axis of the imaging plane is the y axis of the acceleration sensor 103.

For example, when the control section 40 rotates about the axis in the longitudinal direction L of the control section 40, area A rotates about the axis in the longitudinal direction of area A in accordance with the rotation of the control section 40. The acceleration sensor 103 detects the direction g of gravity from the acceleration accompanying the rotation of area A. The acceleration sensor 103 detects the first rotational change quantity of the control section 40 based on the detected direction g of gravity. The first rotational change quantity of the control section 40 detected by the acceleration sensor 103 is always output in real time to the attitude calculator 70 as an electrical signal.

[Correction]

Next, correction of the first rotational change quantity will be described.

In general, it is conceivable that an installation error occurs when the acceleration sensor 103 is installed inside the control section 40. The installation error means that the axis of the acceleration sensor 103 is displaced with respect to the insertion apparatus 20 and, as a result, leads to, for example, a detection error of the first rotational change quantity. Therefore, when the acceleration sensor 103 is installed in the control section 40, for example, in the manufacturing process of the insertion apparatus 20, the axis displacement of the acceleration sensor 103 with respect to the insertion apparatus 20 is measured. For example, the axis displacement of the acceleration sensor 103 is measured based on how much the y axis is tilted with respect to the vertical axis of the image. The first rotational change quantity needs to be corrected so that the measured axis displacement is eliminated.

As shown in FIG. 1, the insertion system 10 includes a correction value storage 41 that stores a correction value for correcting the axis displacement of the attitude detector 100 with respect to the insertion apparatus 20 that occurs when the attitude detector 100 is built in the insertion apparatus 20, and a correction unit 71 that reads therein the correction value and corrects the first rotational change quantity detected by the attitude detector 100 based on the read correction value. The correction value storage 41 is constituted by, for example, a memory or the like. The correction value storage 41 is built in, for example, the insertion apparatus 20. In consideration of the narrow inner space of the insertion section 30, the correction value storage 41 is preferably built in, for example, the control section 40. The correction unit 71 is preferably included in, for example, the attitude calculator 70. The correction value is generally different for each insertion apparatus 20.

In the manufacturing process of the insertion apparatus 20, the correction value storage 41 stores in advance a correction value by an input operation of an external operation device, such as a keyboard (not shown). Alternatively, the correction value may be measured by a measuring instrument (not shown), and input and stored in the correction value storage 41. The correction unit 71 makes a correction, for example, when the insertion apparatus 20 is connected to the main body 60a through the cord 50, and the first rotational change quantity detected by the acceleration sensor 103 is input to the correction unit 71.

Since the correction unit 71 corrects the first rotational change quantity, the accuracy of the first rotational change quantity is improved. Accordingly, the acceleration sensor 103 can be installed in the control section 40 without concern for the axis displacement of the acceleration sensor 103. Therefore, the manufacturing efficiency of the insertion apparatus 20 is improved, and the manufacturing cost of the insertion apparatus 20 is reduced. Since the correction value storage 41 is built in the insertion apparatus 20, the configuration of the main body 60a is simplified. The main body 60a can be shared by insertion apparatuses 20. Note that occurrence of an installation error, axis displacement, and correction are the same regardless of where the attitude detector 100 is installed.

[Calculation]

Next, the calculation by the attitude calculator 70 will be described.

The acceleration sensor 103 detects not only the direction g of gravity, but also the acceleration generated when the insertion apparatus 20 moves. That is, the first rotational change quantity detected by the acceleration sensor 103 and corrected by the correction unit 71 includes, for example, not only gravity information including the direction g of gravity acting on area A, but also the acceleration generated by the movement of the insertion apparatus 20. As shown in FIG. 1, the attitude calculator 70 includes an extraction unit 73 configured to extract only the gravity information from the first rotational change quantity corrected by the correction unit 71 after being detected by the gravity sensor. The extraction unit 73 extracts only the gravity information from the first rotational change quantity by a commonly-known method, such as removing the acceleration from the first rotational change quantity by a low-pass filter. The attitude calculator 70 includes a rotation quantity calculator 75 configured to calculate calculates a second rotational change quantity included in the attitude information of the insertion apparatus 20, based on the gravity information extracted by the extraction unit 73. The second rotational change quantity is a change quantity of the insertion apparatus 20 about the axis in the longitudinal direction of the insertion apparatus 20. Here, the second rotational change quantity is calculated based on only the gravity information. In the attitude calculator 70, the correction unit 71, the extraction unit 73, and the rotation quantity calculator 75 may be constituted by using a single calculation circuit (for example, CPU), or may be constituted by using calculation circuits. In the latter case, the calculation circuits may cooperate with each other by transmitting and receiving data to and from each other. In the latter case, the calculation circuits may also be arranged in different housings.

In the present embodiment, since the attitude detector 100 is built in the control section 40, the second rotational change quantity can be regarded as the change quantity at the control section 40. In the present embodiment, since the entire insertion section 30 follows the rotation of the control section 40, the second rotational change quantity can be regarded as the second rotational change quantity of the entire insertion section 30 and the second rotational change quantity of the entire insertion apparatus 20. The rotation quantity calculator 75 calculates the second rotational change quantity included in the attitude information of the insertion apparatus 20, based on the first rotational change quantity.

Figure 3B:
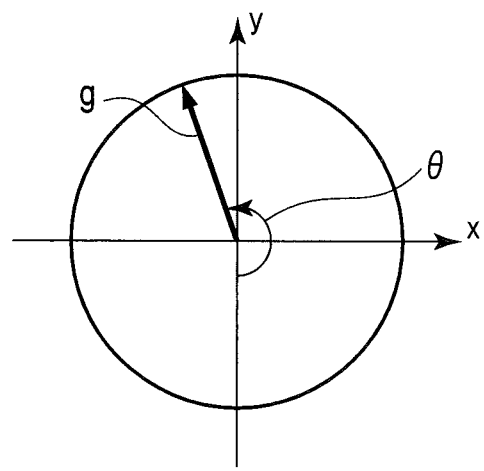
FIG. 3B is a diagram illustrating the second rotational change quantity.

The rotation quantity calculator 75 separates the gravity information into components on the X-Y plane shown in FIGS. 3A and 3B. The acceleration sensor 103 is installed so that the positive direction of the y axis of the acceleration sensor 103 coincides with the positive direction of the vertical axis of the image produced by the imaging device 31a, and in addition, the axis displacement is corrected. When the insertion section 30 is linear and the vertical axis of the imaging plane of the imaging device 31a having the vertical axis and the horizontal axis of the image is arranged perpendicular to the ground, the direction g of gravity included in the gravity information separated into components on the X-Y plane indicates the negative direction of the y axis. Such a state is generally a state that can be easily recognized by the operator when the insertion apparatus 20 is used. Furthermore, the state in which the vertical axis of the imaging plane of the imaging device 31a is arranged perpendicular to the ground is the reference of the second rotational change quantity calculated by the rotation quantity calculator 75, i.e., the state in which the second rotational change quantity is 0 degree. As shown in FIGS. 3A and 3B, the angle θ formed by the negative-side axis of the y axis and the direction g of gravity separated into components on the X-Y plane is the second rotation change quantity of the insertion apparatus 20.

Note that the reference of the second rotational change quantity need not be limited to the state where the imaging plane of the imaging device 31a is arranged perpendicular to the ground. For example, when the second rotational change quantity with respect to the front surface of the subject 15 is needed to be calculated, the reference is, for example, the state of the control section 40 at the time of starting insertion of the insertion apparatus 20 into the subject 15. As described above, the reference may be any state.

In this case, as shown in FIG. 1, the main body 60a includes a reference storage 80 electrically connected to the rotation quantity calculator 75, and the control section 40 includes an instruction device 43, such as a switch, electrically connected to the rotation quantity calculator 75 and the reference storage 80. When a storage instruction output from the instruction device 43 is input to the rotation quantity calculator 75, the reference storage 80 receives the second rotational change quantity calculated by the rotation quantity calculator 75 from the rotation quantity calculator 75 and then stores the received second rotational change quantity as a reference.

Although not shown, when the insertion apparatus 20 is inserted into the subject 15, alignment is performed so that, for example, the longitudinal direction L of the control section 40 is orthogonal to the front surface of the subject 15. In the alignment, for example, the upward direction in which the bendable portion 33 is bent may be aligned with the upper side of the front surface of the subject 15. Next, when the instruction device 43 is pressed, the reference storage 80 stores, as a reference, the second rotational change quantity at the time when the instruction device 43 is pressed, for example, the time of starting insertion. The rotation quantity calculator 75 calculates the difference between the stored second rotational change quantity at the time of starting insertion and the second rotational change quantity after insertion. Based on the calculation result, the rotation quantity calculator 75 calculates the second rotational change quantity with reference to the time of starting insertion. As described above, the rotation quantity calculator 75 calculates the current second rotational change quantity with reference to the second rotational change quantity at the time of starting insertion, which is stored in the reference storage 80.

That is, when the attitude calculator 70 calculates the second rotational change quantity, which is attitude information of the insertion apparatus 20 with respect to the subject 15, the insertion apparatus 20 at the time of, for example, starting insertion is aligned with the subject 15. Next, the reference storage 80 stores attitude information of the insertion apparatus 20 at the time of alignment as a reference when receiving a storage instruction from the instruction device 43. Based on the difference between the attitude information of the insertion apparatus 20 detected later and the stored attitude information of the insertion apparatus 20, the attitude calculator 70 calculates attitude information of the insertion apparatus 20 with respect to the subject 15.

Figure 4:
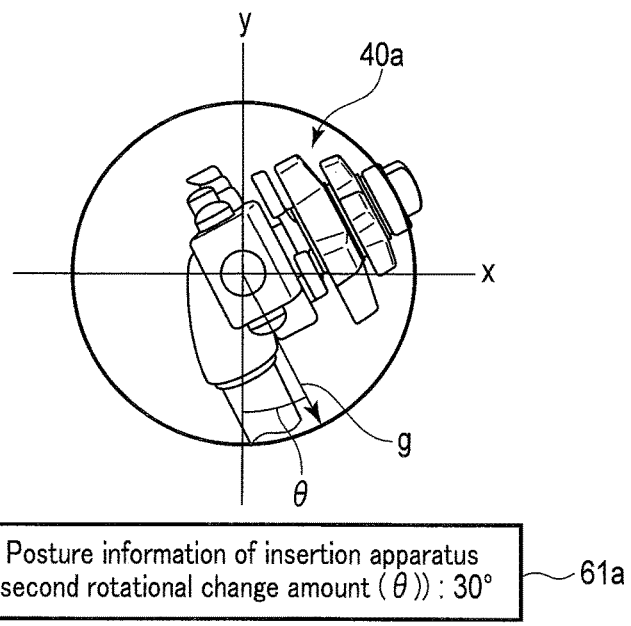
FIG. 4 is a diagram showing a display example of the second rotational change quantity.

As shown in, for example, FIG. 4, the display 60b displays the coordinate system on the X-Y plane, the direction g of gravity separated into components on the X-Y plane, the second rotational change quantity (attitude information of the insertion apparatus 20), which is the angle θ formed by the negative-side axis of the y axis and the direction g of gravity, and a top view 40a of the control section 40. For example, the display 60b displays the second rotational change quantity as a numerical value 61a and displays the coordinate system on the X-Y plane, the direction g of gravity, and the top view 40a of the control section 40 with overlapping them. Therefore, the operator becomes aware of the attitude information of the insertion apparatus 20.

In the present embodiment, the attitude detector 100 is built in the insertion apparatus 20, and detects the first rotational change quantity. The attitude calculator 70 calculates the second rotational change quantity included in the attitude information of the insertion apparatus 20, based on the first rotational change quantity. Accordingly, the present embodiment enables reliable and easy detection of attitude information of the insertion apparatus 20. The display 60b displays attitude information of the insertion apparatus 20. Therefore, the operator can easily confirm attitude information of the insertion apparatus 20 without taking their eyes off the display 60b. The operator need not take their eyes off the display 60b to directly view the insertion apparatus 20 to ascertain the attitude information of the insertion apparatus 20. The operator can confirm attitude information of the insertion apparatus 20 while viewing the observation image produced by the imaging device 31a and displayed on the display 60b. The operator can concentrate on the insertion operation of the insertion apparatus 20, and the operability of the insertion apparatus 20 can be improved.

In the present embodiment, since the correction unit 71 corrects the first rotational change quantity, the accuracy of the first rotational change quantity can be improved. Furthermore, the acceleration sensor 103 can be installed in the control section 40 without concern for the axis displacement of the acceleration sensor 103. Therefore, the manufacturing efficiency of the insertion apparatus 20 can be improved, and the manufacturing cost of the insertion apparatus 20 can be reduced.

In the present embodiment, the attitude calculator 70 calculates attitude information of the insertion apparatus 20 based on the first rotational change quantity corrected by the correction unit 71. Therefore, highly-accurate attitude information of the insertion apparatus 20 can be reliably and easily detected.

In the present embodiment, a highly-accurate first rotational change quantity can be detected by the acceleration sensor 103. Note that the first rotational change quantity detected by the acceleration sensor 103 and corrected by the correction unit 71 includes acceleration. However, in the present embodiment, the extraction unit 73 extracts only gravity information from the first rotational change quantity, and the rotation quantity calculator 75 calculates the second rotational change quantity based on the gravity information, not the first rotational change quantity. Therefore, highly-accurate attitude information of the insertion apparatus 20 can be reliably and easily detected.

The rotation quantity calculator 75 of the present embodiment calculates the second rotational change quantity based on gravity information. Therefore, the need for adjustment in which the reference of the second rotational change quantity is set to the ground can be eliminated, and the rotation quantity calculator 75 can always calculate the second rotational change quantity quickly.

In the present embodiment, attitude information of the insertion apparatus 20, which is the change quantity of the current attitude with respect to the reference, can be reliably and easily detected with the aid of the reference storage 80.

According to the above description, the gravity detected by the acceleration sensor 103 is separated into components on the X-Y plane for calculation of the second rotational change quantity; however, the configuration is not limited to this. For example, the direction components of gravity are not limited to those on the X-Y plane, and gravity may be separated into direction components in accordance with attitude information of the insertion apparatus 20 desired to be detected. Furthermore, in the above-described installation of the acceleration sensor 103, the x axis and the y axis are arranged to be orthogonal to the longitudinal direction L of the control section 40; however, the arrangement is not limited to this. For example, the arrangement of the coordinate system in the installation of the acceleration sensor 103 may be determined in accordance with attitude information of the insertion apparatus 20 desired to be detected. Moreover, acceleration sensors 103 may be arranged in accordance with attitude information of the insertion apparatus 20 desired to be detected, and the coordinate systems of the acceleration sensors 103 may be arranged in different directions.

The attitude calculator 70 may be built in the control section 40 or the connector 51.

The correction value storage 41 may be built in the main body 60a. In this case, since the correction value storage 41 need not be built in the insertion apparatus 20 having a limited inner space, the inner space can be effectively utilized, and the manufacturing efficiency of the insertion apparatus 20 can be improved. The operator may cause the correction value storage 41 to store a desired correction value at a desired time by an external operation device, such as a keyboard (not shown). For example, the operator may identify the serial number of the insertion apparatus 20 with a label or the like attached to the insertion apparatus 20, download the correction value corresponding to the serial number from the Web or the like to the correction value storage 41, and cause the correction value storage 41 to store the downloaded correction value. This operator is not limited to the actual operator, but may be a purchaser who has purchased the insertion system 10, a delivery person who delivers to the insertion system 10, or a maintenance person who maintains the insertion system 10. The correction value storage 41 may store correction values for insertion apparatuses 20 and use a correction value by, for example, identifying the serial number, or the like of the insertion apparatus 20.

If the frequency of use of the insertion apparatus 20 increases, the acceleration sensor 103 may be rattled, so that the axis displacement of the acceleration sensor 103 may occur. When the insertion apparatus 20 is connected to the main body 60a, if the main body 60a can measure the axis displacement of the acceleration sensor 103 and the display 60b can display the measurement result, the operator or the maintenance person can cause the correction value storage 41 to store a desired correction value at a desired time by an external operation device, such as a keyboard (not shown). This enables use of the latest correction value suitable for the state of the insertion apparatus 20, further improving the accuracy of the first rotational change quantity. In this case, even when the same insertion apparatus 20 is used, the correction value can be appropriately adjusted in accordance with the use of the insertion apparatus 20.

[Configuration 2 of Attitude Detector 100]

Figure 5:
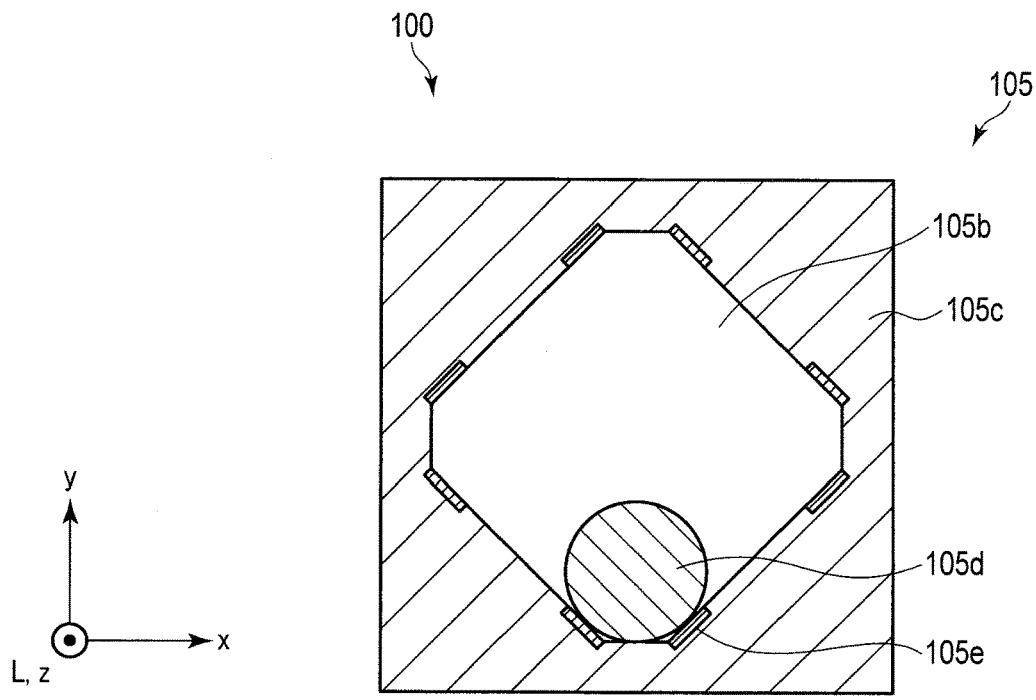
FIG. 5 is a diagram illustrating a weight sensor in the gravity sensor.

Hereinafter, Configuration 2 of the attitude detector 100 will be described with reference to FIG. 5.

Although the gravity sensor includes the acceleration sensor 103 in order to detect the direction g of gravity acting on area A, the gravity sensor does not have to include the acceleration sensor 103 as long as the direction g of gravity acting on area A can be detected. The gravity sensor may include, for example, at least one weight sensor 105. The weight sensor 105 includes a main body 105c having an inner space 105b, a weight member 105d contained in the inner space 105b, and detection members 105e arranged on the inner peripheral surface of the inner space 105b.

The main body 105c may be, for example, the housing of the control section 40 or a member built in the housing.

The weight member 105d is movable in the inner space 105b in accordance with the direction g of gravity that changes as the insertion apparatus 20 rotates about the axis in the longitudinal direction of the insertion apparatus 20 and acts on the attitude detector 100. The weight member 105d is conductive.

The detection members 105e allow detecting the position or direction of the weight member 105d with respect to the insertion apparatus 20 and then detecting the first rotational change quantity of area A (operation section 40) based on the detected position or direction. For example, the detection members 105e allow detecting the position of the weight member 105d or the direction of the weight member 105d by contact of the weight member 105d with the detection members 105e. The weight sensor 105 is configured to detect the direction g of gravity based on the position or direction and then detect the first rotational change quantity of the control section 40 in accordance with the direction g of gravity. The detection members 105e include, for example, electrodes. The inner space 105b is, for example, octagonal, and the detection members 105e are arranged at the eight corners.

The coordinate system of the weight sensor 105 is defined as a right-hand system including an x axis, a y axis orthogonal to the x axis, and a z axis orthogonal to the x axis and the y axis. In this case, the weight sensor 105 is installed inside the control section 40 so that, in a state where the insertion section 30 is linearly arranged, the x axis and the y axis are arranged orthogonally to the longitudinal direction L of the control section 40, and the z axis is arranged along the longitudinal direction L of the control section 40, the y axis is arranged along the vertical axis of the image produced by the imaging device 31a, the positive direction of the y axis coincides with the positive direction of the vertical axis, and the x axis is arranged along the horizontal axis of the image.

When the attitude detector 100 of Configuration 2 is used, for example, a state where the z axis is arranged parallel to the ground is the reference of the first rotational change quantity of the control section 40 detected by the weight sensor 105. The parallel arrangement state indicates a state where the imaging plane of the imaging device 31a having the vertical axis and the horizontal axis of the image is arranged perpendicular to the ground.

For example, when the control section 40 rotates about the axis in the longitudinal direction L of the control section 40, area A rotates about the axis in the longitudinal direction of area A in accordance with the rotation of the control section 40. The weight member 105d moves in the inner space 105b due to gravity that changes in accordance with the rotation of the control section 40, and comes into contact with a pair of detection members 105e. The weight sensor 105 detects the position of the weight member 105d or the direction of the weight member 105d by contact of the weight member 105d with the detection members 105e. Next, the weight sensor 105 detects the direction g of gravity based on the position or direction. Finally, the weight sensor 105 detects the first rotational change quantity of the control section 40 in accordance with the direction g of gravity. The first rotational change quantity of the control section 40 detected by the weight sensor 105 is always output in real time to the attitude calculator 70 as an electrical signal.

Correction of the first rotational change quantity in Configuration 2 of the attitude detector 100 is the same as that of the acceleration sensor 103 (Configuration 1 of the attitude detector 100). In addition, the weight sensor 105 detects only gravity information (components on the X-Y plane in the direction of gravity) because of its structure. Therefore, in the calculation by the attitude calculator 70 for the weight sensor 105, separation of gravity information (direction components of gravity) is unnecessary. Since the other part of the calculation is the same as that for the acceleration sensor 103, a description thereof is omitted here.

The inner space 105b is, for example, octagonal, and the detection members 105e are arranged at the eight corners. Therefore, the weight sensor 105 is configured to detect four directions g of gravity. However, the shape of the inner space 105b, the number of the detection members 105e, and the arrangement positions of the detection members 105e may be changed in accordance with the resolution of the rotation quantity desired to be detected.

The weight sensor 105 may detect the position or the direction of the weight member 105d by another method using, for example, light or magnetism instead of electricity.

Configuration 2 of the attitude detector 100 can provide the same effects as Configuration 1 of the attitude detector 100.

[Configuration 3 of Attitude Detector 100]

Figure 6:
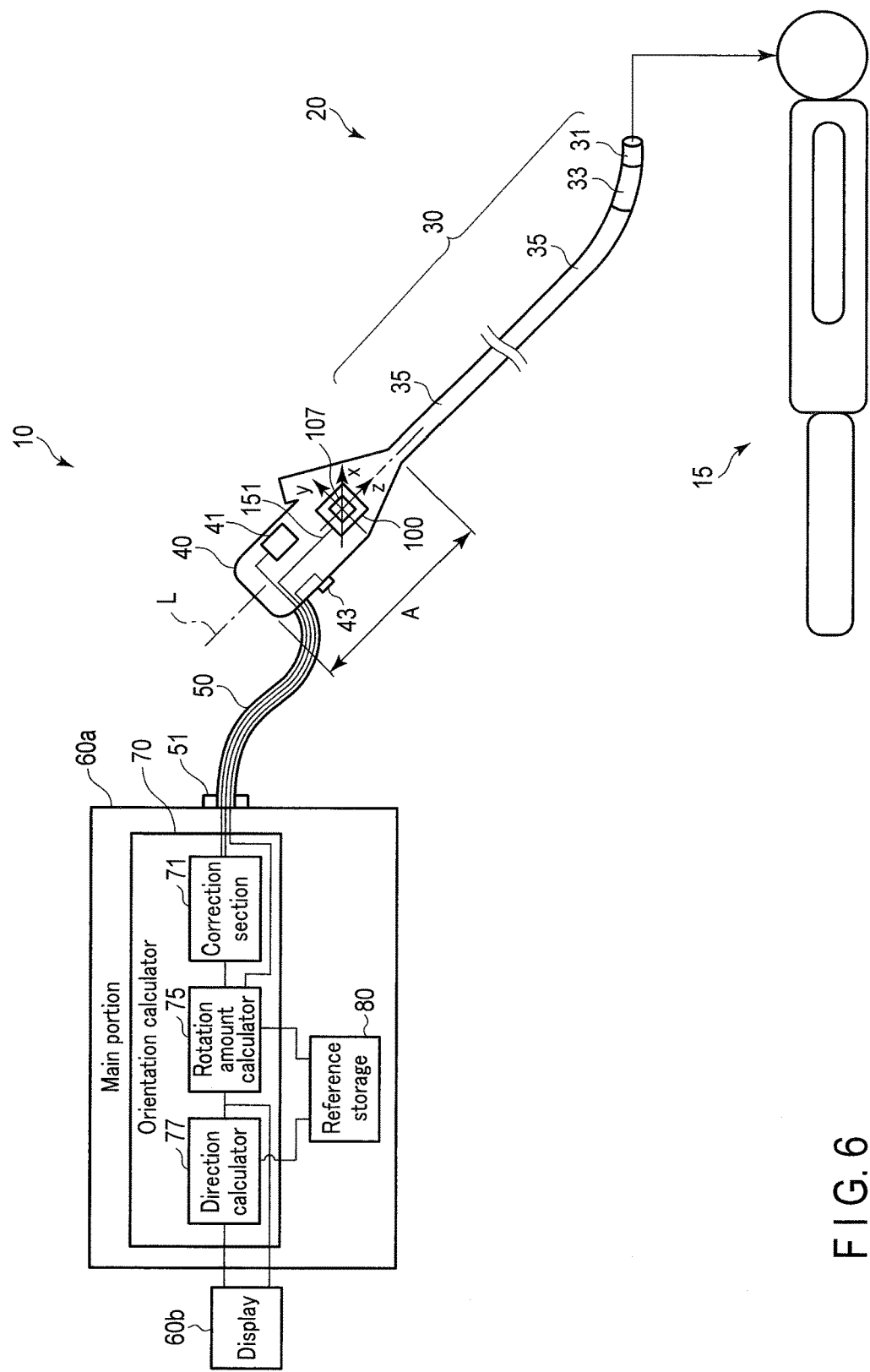
FIG. 6 is a schematic diagram of an insertion system including a gyro sensor.

Hereinafter, Configuration 3 of the attitude detector 100 will be described with reference to FIG. 6.

The attitude detector 100 may include a gyro sensor 107 configured to detect the angular velocity of area A and then detect at least one of the first rotational change quantity and the first directional change quantity on the detected angular velocity. Since the attitude detector 100 is built in the control section 40, the angular velocity of area A can be regarded as the angular velocity of the control section 40. The gyro sensor 107 is, for example, of an electrostatic capacitance type or a piezo type manufactured by MEMS technology. The gyro sensor 107 is, for example, a three-axis sensor.

Here, the coordinate system of the gyro sensor 107 is defined as a right-hand system including an x axis, a y axis orthogonal to the x axis, and a z axis orthogonal to the x axis and the y axis. In this case, the gyro sensor 107 is installed inside the control section 40 so that, in a state where the insertion section 30 is linearly arranged, the x axis and the y axis are arranged orthogonally to the longitudinal direction L of the control section 40, and the z axis is arranged along the longitudinal direction L of the control section 40, the y axis is arranged along the vertical axis of the image produced by the imaging device 31a, the positive direction of the y axis coincides with the positive direction of the vertical axis, and the x axis is arranged along the horizontal axis of the image. The positive direction of the y axis coinciding with the positive direction of the vertical axis means that the positive direction of the y axis coincides with the upward direction of the image displayed on the display 60b.

The gyro sensor 107 detects, for example, the angular velocity about the longitudinal (Z) axis of the control section 40, the angular velocity about the x axis, and the angular velocity about the y axis. The gyro sensor 107 is configured to detect the first rotational change quantity about the longitudinal (Z) axis of the control section 40 based on the angular velocity about the longitudinal (Z) axis. The gyro sensor 107 is configured to detect a first X rotational change quantity about the x axis at the control section 40 based on the angular velocity about the x axis. The gyro sensor 107 is also configured to detect a first Y rotational change quantity about the y axis at the control section 40 based on the angular velocity about the y axis. The first X rotational change quantity and the first Y rotational change quantity are included in the change quantity (hereinafter referred to as a first orthogonal rotational change quantity) of the control section 40 about the direction orthogonal to the longitudinal direction L of the control section 40 (attitude detector 100), and are included in the attitude information of the control section 40. That is, the gyro sensor 107 detects, on the detected angular velocity, the first rotational change quantity and the first orthogonal rotational change quantity about the direction orthogonal to the longitudinal direction L of the control section 40 (area A). The first orthogonal rotational change quantity is the detected angular velocity. The first rotational change quantity, first X rotational change quantity, and first Y rotational change quantity detected by the gyro sensor 107 are always output in real time to the attitude calculator 70 as an electrical signal.

To detect the rotation by the gyro sensor 107, the reference of the first rotational change quantity and the first orthogonal rotational change quantity, i.e., the state where the first rotational change quantity and the first orthogonal rotational change quantity are 0 degrees, needs to be determined. The rotation quantity detected and calculated at a given position in a state where the reference has not been determined is based on, for example, the time when the insertion system 10 is powered on and the operation of the insertion system 10 is started. The attitude of the insertion apparatus 20 at the time of starting the operation of the insertion system 10 is unclear to the operator and not suitable as a reference. The reference is a given state, such as the state of the control section 40 at the time of starting insertion of the insertion apparatus 20 into the subject 15. This reference corresponds to the time when the instruction device 43 is pressed and a storage instruction is input from the instruction device 43 to the rotation quantity calculator 75.

When the insertion apparatus 20 is inserted into the subject 15, the instruction device 43 is pressed. As a result, when a storage instruction output from the instruction device 43 is input to the rotation quantity calculator 75, the reference storage 80 stores a second rotational change quantity, a second X rotational change quantity, and a second Y rotational change quantity (to be described later) input from the rotation quantity calculator 75 as a reference.

Note that the attitude calculator 70 may start integration of the angular velocity when the instruction output from the instruction device 43 is input to a direction calculator 77 to be described later. As a result, the second rotational change quantity, second X rotational change quantity, and second Y rotational change quantity of the angle are calculated with reference to the time when the instruction output from the instruction device 43 is input to the direction calculator 77. In this case, the reference storage 80 is unnecessary.

[Correction]

The correction unit 71 corrects the first rotational change quantity detected by the attitude detector 100, based on a correction value. Since correction of the first rotational change quantity in Configuration 3 of the attitude detector 100 is the same as that of the acceleration sensor 103 (Configuration 1 of the attitude detector 100), a detailed description thereof is omitted here. The correction unit 71 corrects the first X rotational change quantity and first Y rotational change quantity detected by the attitude detector 100, based on the correction value. Since correction of the first X rotational change quantity and that of the first Y rotational change quantity are the same as that of the first rotational change quantity, a detailed description thereof is omitted here.

[Calculation]

Next, the calculation by the attitude calculator 70 will be described.

The attitude calculator 70 includes a rotation quantity calculator 75 configured to calculate a second rotational change quantity included in attitude information of the insertion apparatus 20, based on the first rotational change quantity corrected by the correction unit 71 after being detected by the gyro sensor 107. Specifically, the rotation quantity calculator 75 calculates the second rotational change quantity by integrating the first rotational change quantity, i.e., the angular velocity from the reference to convert it into an angle. For example, when the control section 40 rotates about the axis in the longitudinal (Z) direction L after the instruction device 43 is pressed, the first rotational change quantity detected by the gyro sensor 107 and corrected by the correction unit 71 is input to the attitude calculator 70. The rotation quantity calculator 75 calculates the second rotational change quantity based on the first rotational change quantity at the reference time and the current first rotational change quantity.

The rotation quantity calculator 75 calculates a second orthogonal rotational change quantity included in the attitude information of the insertion apparatus 20, based on the first orthogonal rotational change quantity corrected by the correction unit 71 after being detected by the gyro sensor 107. The second orthogonal rotational change quantity is the change quantity of the insertion apparatus 20 about the direction orthogonal to the longitudinal direction of the insertion apparatus 20. The second orthogonal rotational change quantity includes the second X rotational change quantity and the second Y rotational change quantity to be described later, and is included in the attitude information of the insertion apparatus 20.

That is, the rotation quantity calculator 75 calculates the second X rotational change quantity, which is the change quantity about the x axis of the insertion apparatus 20, based on the first X rotational change quantity corrected by the correction unit 71 after being detected by the gyro sensor 107. Specifically, the rotation quantity calculator 75 calculates the second X rotational change quantity by integrating the first X rotational change quantity from the reference. For example, when the control section 40 rotates about the axis in the X direction after the instruction device 43 is pressed, the first X rotational change quantity detected by the gyro sensor 107 and corrected by the correction unit 71 is input to the attitude calculator 70. The rotation quantity calculator 75 calculates the second X rotational change quantity with respect to the reference from the difference between the second X rotational change quantity at the reference time and the current second X rotational change quantity.

Note that the rotation quantity calculator 75 may perform at least one of calculation of the second X rotational change quantity and calculation of the second X orthogonal rotational change quantity.

The rotation quantity calculator 75 calculates the second Y rotational change quantity in a manner similar to the second X rotational change quantity.

In Configuration 3, since the attitude detector 100 is built in the control section 40, the second orthogonal rotational change quantity can be regarded as the change quantity at the control section 40. The rotation quantity calculator 75 calculates the second orthogonal rotational change quantity included in the attitude information of the control section 40, based on the first orthogonal rotational change quantity.

The attitude calculator 70 includes a direction calculator 77 configured to calculate a second directional change quantity included in the attitude information of the control section 40, based on the second X rotational change quantity and second Y rotational change quantity included in the second orthogonal rotational change quantity calculated by the rotation quantity calculator 75. The second directional change quantity is the change quantity of the control section 40 in the longitudinal direction of the control section 40.

In Configuration 3, since the attitude detector 100 is built in the control section 40, the second directional change quantity can be regarded as the change quantity at the control section 40.

The attitude calculator 70 calculates at least one of the second rotational change quantity of the control section 40 and the second directional change quantity of the control section 40 that are included in the attitude information of the control section 40, based on the angular velocity detected by the gyro sensor 107.

The reference need not be limited to a state at the time of starting insertion of the insertion apparatus 20 into the subject 15, but may be a state at a desired time when the instruction device 43 is pressed. The desired time is, for example, when the insertion apparatus 20 reaches the entrance of an organ after starting insertion of the insertion apparatus 20 into the subject 15. In this case, when a storage instruction output from the instruction device 43 is input to the rotation quantity calculator 75, the reference storage 80 receives the second rotational change quantity calculated by the rotation quantity calculator 75 from the rotation quantity calculator 75 to store the received second rotational change quantity as a reference. That is, the reference storage 80 stores the second rotational change quantity at a desired time as a reference.

The rotation quantity calculator 75 calculates the attitude change quantity with respect to the reference based on the second rotational change quantity of the control section 40 at a desired time and the current second rotational change quantity of the control section 40 after the desired time. The rotation quantity calculator 75 calculates the current second rotational change quantity with reference to the second rotational change quantity of the control section 40 at the desired time that is stored in the reference storage 80.

When a storage instruction output from the instruction device 43 is input to the rotation quantity calculator 75, the reference storage 80 receives, from the rotation quantity calculator 75, the second X rotational change quantity and second Y rotational change quantity calculated by the rotation quantity calculator 75 to store the second X rotational change quantity and second Y rotational change quantity, and receives, from the direction calculator 77, the second directional change quantity calculated by the direction calculator 77 and stores the second directional change quantity.

The rotation quantity calculator 75 calculates the current second X rotational change quantity and second Y rotational change quantity with reference to the second X rotational change quantity and second Y rotational change quantity of the control section 40 at a desired time that are stored in the reference storage 80. The direction calculator 77 calculates the current second directional change quantity with reference to the second directional change quantity of the control section 40 at a desired time that is stored in the reference storage 80.

The reference storage 80 may store the first rotational change quantity and first orthogonal rotational change quantity detected by the gyro sensor 107 as a reference.

In Configuration 3, the attitude detector 100 is built in the insertion apparatus 20 and detects the first rotational change quantity. Based on the first rotational change quantity, the attitude calculator 70 calculates at least one of the second rotational change quantity and second directional change quantity of the insertion apparatus 20 included in the attitude information of the insertion apparatus 20. Accordingly, the present embodiment enables reliable and easy detection of attitude information of the insertion apparatus 20. The display 60b displays attitude information of the insertion apparatus 20. Therefore, the operator can easily confirm attitude information of the insertion apparatus 20 without taking their eyes off the display 60b. The operator need not take their eyes off the display 60b to directly view the insertion apparatus 20 to ascertain the attitude information of the insertion apparatus 20. The operator can confirm attitude information of the insertion apparatus 20 while viewing the observation image produced by the imaging device 31a and displayed on the display 60b. The operator can concentrate on the insertion operation of the insertion apparatus 20, and the operability of the insertion apparatus 20 can be improved.

In Configuration 3, since the correction unit 71 corrects the first rotational change quantity and the first orthogonal rotational change quantity, the accuracy of the first rotational change quantity and the accuracy of the first orthogonal rotational change quantity can be improved. Furthermore, the gyro sensor 107 can be installed in the control section 40 without concern for the axis displacement of the gyro sensor 107. The manufacturing efficiency of the insertion apparatus 20 can be improved, and the manufacturing cost of the insertion apparatus 20 can be reduced.

In Configuration 3, the attitude calculator 70 calculates attitude information of the insertion apparatus 20 based on the first rotational change quantity and first orthogonal rotational change quantity corrected by the correction unit 71. Therefore, highly-accurate attitude information of the insertion apparatus 20 can be reliably and easily detected.

In Configuration 3, a highly-accurate first rotational change quantity and first orthogonal rotational change quantity can be detected by the gyro sensor 107. Therefore, the present embodiment enables reliable and easy detection of highly-accurate attitude information of the insertion apparatus 20.

In Configuration 3, attitude information of the insertion apparatus 20, which is the change quantity of the current attitude with respect to the reference, can be reliably and easily detected with the aid of the reference storage 80.

The description has been provided using the three-axis gyro sensor 107 as an example; however, the gyro sensor 107 is not limited to this, and a gyro sensor 107 having a number of axes necessary for detection may be used.

[Configuration 4 of Attitude Detector 100]

Hereinafter, Configuration 4 of the attitude detector 100 will be described with reference to FIG. 7.

The attitude detector 100 may include an acceleration sensor 103 and a gyro sensor 107. The acceleration sensor 103 detects the direction g of gravity; when the insertion apparatus 20 rotates about the axis in the direction g of gravity, the direction g of gravity does not change. Therefore, the acceleration sensor 103 cannot perform detection, so that the attitude calculator 70 cannot calculate attitude information of the insertion apparatus 20. On the other hand, when rotation is detected using the gyro sensor 107, since the angular velocity is integrated to calculate the angle, errors may be accumulated in the calculated second rotational change quantity.

Therefore, when the insertion apparatus 20 rotates about an axis other than the axis in the direction g of gravity, the acceleration sensor 103, which does not cause accumulation of errors, performs detection. When the insertion apparatus 20 rotates about the axis in the direction g of gravity, since the acceleration sensor 103 cannot perform detection, the gyro sensor 107 performs detection. The gyro sensor 107 compensates detection until the insertion apparatus 20 again rotates about an axis other than the axis in the direction g of gravity. Even if errors are accumulated during this compensation, the accumulated errors are eliminated if the insertion apparatus 20 rotates again about an axis other than the axis in the direction g of gravity, and the acceleration sensor 103 performs detection again. In this way, usually using the acceleration sensor 103 enables calculation of the highly-accurate second rotational change quantity of the control section 40 without accumulated errors. When the insertion apparatus 20 rotates about the axis of the direction g of gravity, although the acceleration sensor 103 cannot be used, the second rotational change quantity of the control section 40 is calculated by using the gyro sensor 107. That is, detection is continued.

Note that the acceleration sensor 103 and the gyro sensor 107 may be configured to detect the first orthogonal rotational change quantity. The attitude calculator 70 may be configured to calculate the second orthogonal rotational change quantity based on the first orthogonal rotational change quantity detected by the acceleration sensor 103 when the insertion apparatus 20 is not rotating about the axis in the direction g of gravity. The attitude calculator 70 may be configured to calculate the second orthogonal rotational change quantity based on the first orthogonal rotational change quantity detected by the gyro sensor 107 when the insertion apparatus 20 is rotating about the axis in the direction g of gravity. The gravity sensor may detect at least one of the first rotational change quantity and the first orthogonal rotational change quantity, and the gyro sensor 107 may detect at least one of the first rotational change quantity and first orthogonal rotational change quantity in the angular velocity of area A. Therefore, the attitude calculator 70 compensates the second rotational change quantity or second orthogonal rotational change quantity calculated based on the first rotational change quantity or first orthogonal rotational change quantity detected by the gravity sensor with the second rotational change quantity or second orthogonal rotational change quantity calculated based on the first rotational change quantity or first orthogonal rotational change quantity detected by the gyro sensor 107.

Configuration 4 can provide the same effects as Configurations 1 and 3.

[Configuration 5 of Attitude Detector 100]

Hereinafter, Configuration 5 of the attitude detector 100 will be described with reference to FIGS. 8A and 8B.

The attitude detector 100 may include a terrestrial magnetism sensor 109 configured to detect the direction of the terrestrial magnetism and then detect the first directional change quantity based on the detected direction of the terrestrial magnetism. The terrestrial magnetism sensor 109 is, for example, a magneto-resistive (hereinafter MR) element, a magneto-impedance (hereinafter MI) element, or a Hall element, and has three axes.

The coordinate system of the terrestrial magnetism sensor 109 is defined as a right-hand system including an x axis, a y axis orthogonal to the x axis, and a z axis orthogonal to the x axis and the y axis. Normally, the operator often wants to know which way the distal end of the insertion section 30 is directed. For this reason, the terrestrial magnetism sensor 109 is installed inside the distal end of the insertion section 30 with the directions of the coordinate system of the terrestrial magnetism sensor 109 being arranged to be the same as, for example, those of the coordinate system of the acceleration sensor 103. However, the installation position of the terrestrial magnetism sensor 109 may be changed depending on the position of the insertion apparatus 20 whose direction is desired to be detected.

Before the terrestrial magnetism sensor 109 detects the terrestrial magnetism, the reference of the first directional change quantity, i.e., the state where the first directional change quantity is 0 degrees, needs to be determined. The reference is a given state, such as the state of the insertion section 30 at the time of starting insertion of the insertion apparatus 20 into the subject 15. This reference corresponds to the time when the instruction device 43 is pressed and a storage instruction is input from the instruction device 43 to the direction calculator 77.

The terrestrial magnetism sensor 109 detects the direction of the terrestrial magnetism with three axes, and detects the first directional change quantity based on the detected direction of the terrestrial magnetism. The first directional change quantity of the insertion section 30 detected by the terrestrial magnetism sensor 109 is always output in real time to the attitude calculator 70 as an electrical signal.

[Correction]

The correction unit 71 corrects the first directional change quantity detected by the attitude detector 100 based on a correction value. Since correction of the first directional change quantity in Configuration 5 of the attitude detector 100 is similar to that of the acceleration sensor 103 (Configuration 1 of the attitude detector 100), a detailed description thereof is omitted here.

[Calculation]

Next, the calculation by the attitude calculator 70 will be described.

The attitude calculator 70 includes a direction calculator 77 configured to calculate a second directional change quantity included in the attitude information of the insertion apparatus 20, based on the first directional change quantity corrected by the correction unit 71 after being detected by the terrestrial magnetism sensor 109. The second directional change quantity is the directional change quantity of the insertion apparatus 20 in the longitudinal direction of the insertion apparatus 20.

The reference need not be limited to a state at the time of starting insertion of the insertion apparatus 20 into the subject 15, but may be a state at a desired time when the instruction device 43 is pressed. The desired time is, for example, when the insertion apparatus 20 reaches the entrance of an organ after starting insertion of the insertion apparatus 20 into the subject 15. In this case, when a storage instruction output from the instruction device 43 is input to the direction calculator 77, the reference storage 80 receives the second directional change quantity calculated by the direction calculator 77 from the direction calculator 77 to store the received second directional change quantity as a reference. That is, the reference storage 80 stores the second directional change quantity at a desired time as a reference.

The direction calculator 77 calculates the attitude change quantity with respect to the reference based on the second directional change quantity of the insertion section 30 at a desired time and the current second directional change quantity of the insertion section 30 after the desired time. As described above, the direction calculator 77 calculates the current second directional change quantity with reference to the second directional change quantity of the insertion section 30 at a desired time that is stored in the reference storage 80.

Since the correction unit 71 corrects the first directional change quantity, the accuracy of the first directional change quantity can be improved. Furthermore, in Configuration 5, the terrestrial magnetism sensor 109 can be installed in the insertion section 30 without concern for the axis displacement of the terrestrial magnetism sensor 109. Therefore, the manufacturing efficiency of the insertion apparatus 20 can be improved, and the manufacturing cost of the insertion apparatus 20 can be reduced.

In Configuration 5, a highly-accurate first directional change quantity can be detected by the terrestrial magnetism sensor 109. Therefore, in Configuration 5, highly-accurate attitude information of the insertion apparatus 20 can be reliably and easily detected.

The direction calculator 77 of Configuration 5 calculates the second directional change quantity based on the direction of the terrestrial magnetism. Therefore, the need for adjustment of the reference of the second directional change quantity to the ground can be eliminated, and the second directional change quantity can always be calculated quickly.

Figure 8B:
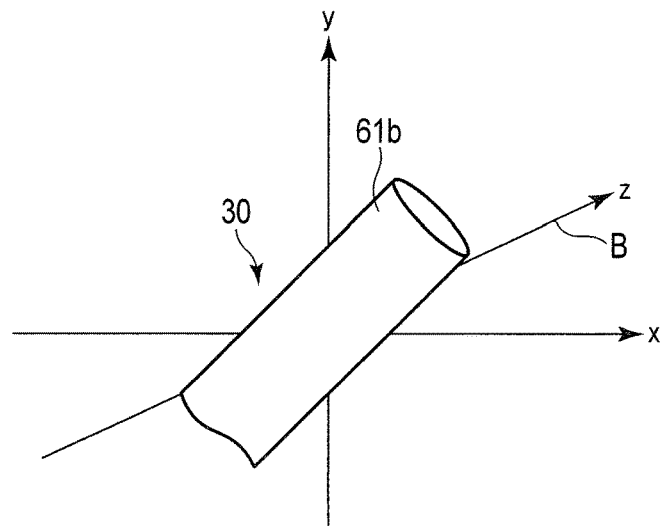
FIG. 8B is a diagram showing a display example of the second directional change quantity.

In Configuration 5, the display 60b displays the second directional change quantity 61b, which is the attitude information of the insertion apparatus 20, in 3D, as shown in FIG. 8B, so that the operator can easily understand the second directional change quantity with respect to the reference direction B. Note that the reference direction displayed on the display 60b is the direction calculated by the direction calculator 77 when a detection instruction of the instruction device 43 is input to the reference storage 80, and corresponds to the z axis of the coordinate system displayed on the display 60b shown in FIG. 8B.

The description has been provided using the three-axis terrestrial magnetism sensor 109 as an example; however, the terrestrial magnetism sensor 109 is not limited to this, and a terrestrial magnetism sensor 109 having a number of axes necessary for detection may be used.

[Summary]

As the configuration of the attitude detector 100 according to the present embodiment, Configurations 1 to 5 of the attitude detector 100 have been described; however, the configuration need not be limited to this. Here, it is assumed that a rotation sensor includes, for example, at least one of the gravity sensor and the gyro sensor 107, and a direction sensor includes, for example, at least one of the gyro sensor 107 and the terrestrial magnetism sensor 109.

The attitude detector 100 is configured to detect the first rotational change quantity by the rotation sensor. The attitude detector 100 is configured to detect the first directional change quantity by the direction sensor. The attitude detector 100 is configured to detect the first rotational change quantity and the first directional change quantity by the rotation sensor and the direction sensor. In this manner, depending on the sensors, the attitude detector 100 is configured to detect at least one of the first rotational change quantity and the first directional change quantity. The attitude calculator 70 calculates attitude information of the insertion apparatus 20 based on at least one of the first rotational change quantity and the first directional change quantity detected by the attitude detector 100. The correction unit 71 corrects at least one of the first rotational change quantity and first directional change quantity detected by the attitude detector 100 based on a correction value. The attitude calculator 70 calculates attitude information of the insertion apparatus 20 based on at least one of the first rotational change quantity and first directional change quantity detected by the attitude detector 100 and corrected by the correction unit 71.

In the present embodiment, the acceleration sensor 103, the gyro sensor 107, and the terrestrial magnetism sensor 109 may be arranged.

[First Modification]

A first modification of the present embodiment will be described with reference to FIG. 9.

The attitude detector 100 may be provided in and near the range of the insertion apparatus 20 of which attitude information is desired to be detected. Such a range is arranged, for example, between the distal end of the insertion section 30 and the proximal end of the insertion section 30.

It is assumed that attitude detectors 100 are arranged in the insertion apparatus 20, as shown in FIG. 9. The attitude calculator 70 may calculate attitude information of the insertion apparatus 20 based on at least one of the first rotational change quantity and first directional change quantity detected by each of the attitude detectors 100. This enables reliable and easy detection of attitude information of each part, such as the hard distal end 31, the flexible tube 35, or the control section 40.

Although not shown, the arrangement position of the attitude detector 100 is not particularly limited as long as the attitude change in the range of which attitude information is desired to be actually detected follows the attitude change in area A. For example, if this range corresponds to the insertion section 30 and the insertion section 30 follows the attitude change of the control section 40, the attitude detector 100 may be arranged in the control section 40.

Although not shown, attitude detectors 100 may be arranged over a range of which attitude information is desired to be detected (for example, the entire insertion section 30).

Although not shown, when attitude detectors 100 are arranged, it is not necessary that all the attitude detectors 100 have three axes, and each attitude detector 100 only has to have the number of axes necessary for detection.

It is assumed that attitude detectors 100 are arranged at different positions in the insertion apparatus 20 along the longitudinal direction of the insertion apparatus 20. In this case, attitude detectors 100 adjacent to one another in the longitudinal direction may function as one unit. As a result, missing axes are compensated for in the unit, and the detection accuracy of attitude information of the insertion apparatus 20 is improved.

[Second Modification]

A second modification of the present embodiment will be described with reference to FIGS. 10A, 10B, 10C, and 10D.

The flexible tube 35 of the present modification does not have rotation followability. That is, a part of the flexible tube 35 does not follow the rotation of another part of the flexible tube 35. In other words, the rotation quantity of a part is different from the rotation quantity of another part, which causes a twist.

In this modification, attitude detectors 100 are arranged. The number of attitude detectors 100 is, for example, three, and they are referred to as attitude detectors 100a, 100b, and 100c, respectively. The attitude detectors 100a, 100b, and 100c are arranged in the flexible tube 35 at different positions in order to detect the quantity of twist of the flexible tube 35 in the longitudinal direction of the flexible tube 35. Specifically, the attitude detectors 100a, 100b, and 100c are arranged at positions of different rotation quantities of the flexible tube 35. For example, the attitude detector 100a is arranged on the control section 40 side, the attitude detector 100c is arranged on the hard distal end 31 side, and the attitude detector 100b is arranged between the attitude detectors 100a and 100c. Here, it is assumed that the attitude detectors 100a, 100b, and 100c each include the acceleration sensor 103.

Figure 10A:
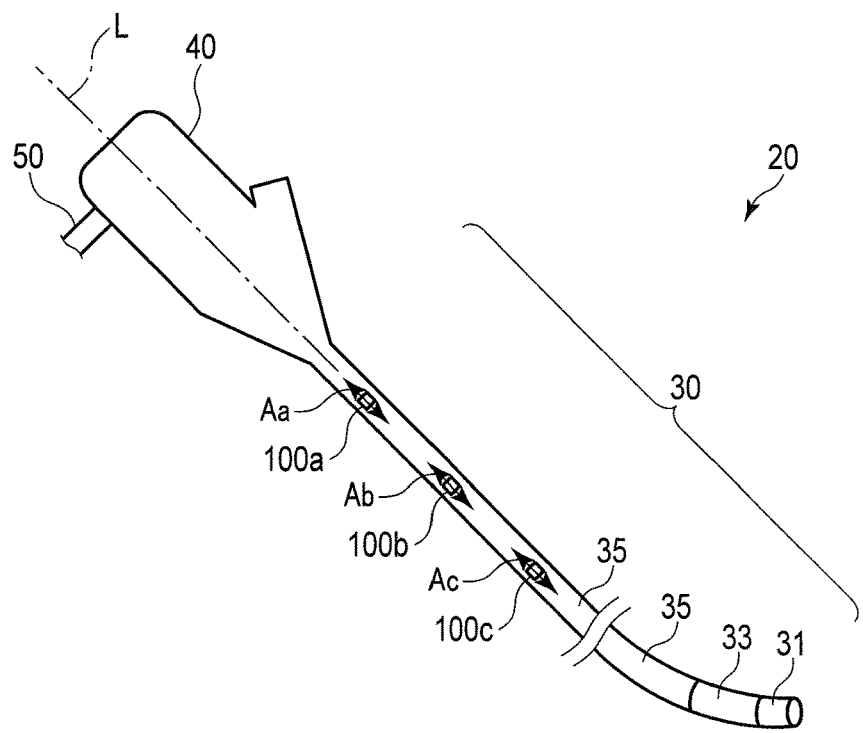
FIG. 10A is a diagram showing a second modification of the first embodiment, and illustrating the quantity of twist in the insertion section.
Figure 10B:
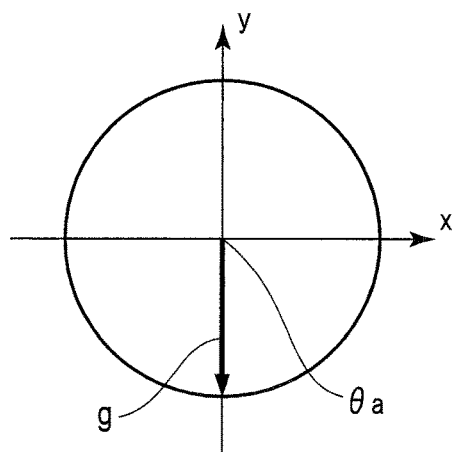
FIG. 10B is a diagram illustrating second rotational change quantity $\theta a$.

Areas A of the attitude detectors 100a, 100b, and 100c are referred to as areas Aa, Ab, and Ac, respectively. Areas Aa, Ab, and Ac are minute areas. As shown in FIGS. 10B, 10C, and 10D, the second rotational change quantities calculated by the attitude calculator 70 based on the first rotational change quantities of areas Aa, Ab, and Ac are referred to as second rotational change quantities θa, θb, and θc, respectively. As in FIGS. 3A and 3B, the second rotational change quantities θa, θb, and θc each indicate the angle formed by the negative-side axis of the y axis and the direction g of gravity separated into components on the X-Y plane.

The attitude calculator 70 calculates a twist of the flexible tube 35 based on the second rotational change quantities θa, θb, and θc. For example, the attitude calculator 70 calculates the quantity of twist of the flexible tube 35 based on the difference between the second rotational change quantities θa and θb and the difference between the second rotational change quantities θb and θc. Note that it the attitude calculator 70 only has to calculate at least the quantity of twist based on the difference between the second rotational change quantities calculated based on the first rotational change quantities detected by adjacent attitude detectors 100. The calculation method is not particularly limited, but, for example, an equation that linearly approximates the second rotational change quantities θa, θb, and θc, or other polynomials may be used.

In the present modification, calculation of the quantity of twist enables detailed, reliable, and easy detection of attitude information of the insertion apparatus 20. The quantity of twist displayed on the display 60b enables the operator to easily ascertain the quantity of twist, and can improve operability.

[Third Modification]

Figure 11A:
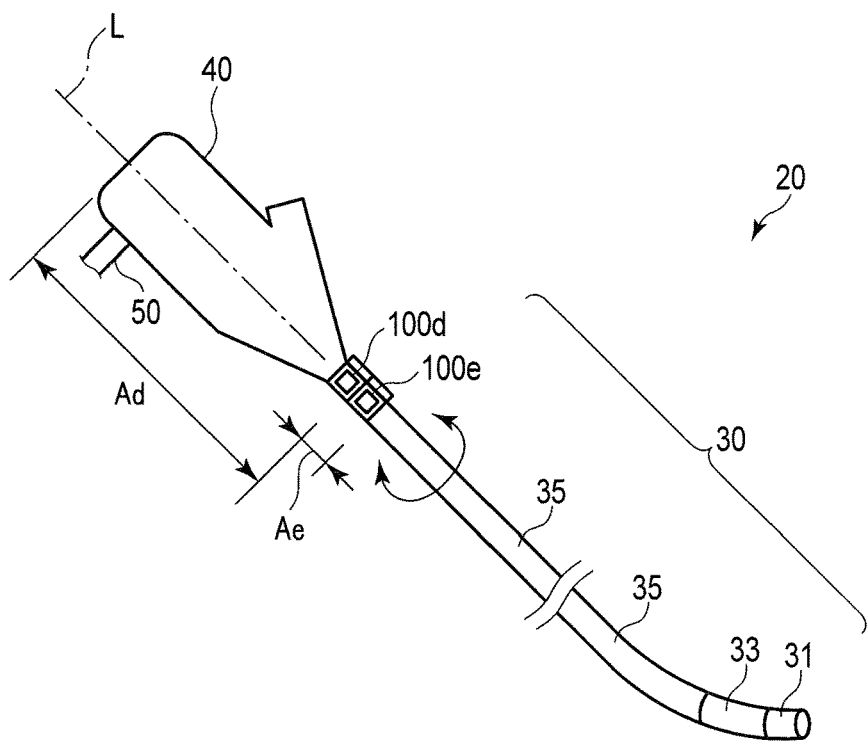
FIG. 11A is a diagram showing a third modification of the first embodiment, and illustrating the quantity of twist of the insertion section with respect to the control section.
Figure 11B:
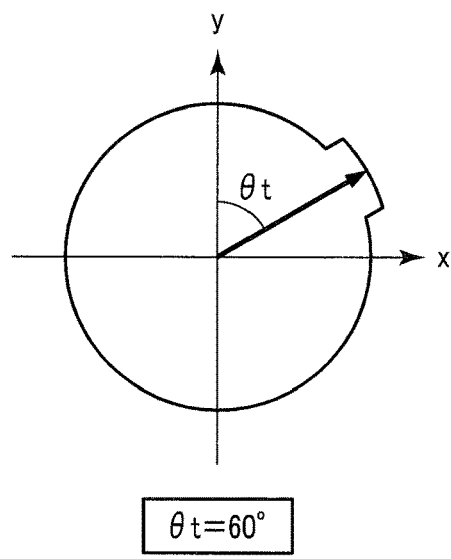
FIG. 11B is a diagram showing a display example of the quantity of twist shown in FIG. 11A.

A third modification of the present embodiment will be described with reference to FIGS. 11A and 11B.

Depending on the type of the insertion apparatus 20, the insertion apparatus 20 has, as one of the operation functions, a function of independently rotating the insertion section 30 about the axis in the longitudinal direction of the insertion apparatus 20 with respect to the control section 40 to change the direction of the bendable portion 33 and the imaging direction of the imaging device 31a. Since the control section 40 gripped by the operator is not rotated, this function enables the operator to stably grip the control section 40. The insertion apparatus 20 that enables such an operation is, for example, a bronchoscope.

In this case, the attitude detectors 100 are arranged in, for example, the control section 40 and the proximal end of the insertion section 30. The attitude detector 100 arranged in the control section 40 is referred to as an attitude detector 100d, and the attitude detector 100 arranged in the proximal end of the insertion section 30 is referred to as an attitude detector 100e. Areas A of the attitude detectors 100d and 100e are referred to as areas Ad and Ae, respectively. Area Ad extends over the entire control section 40, and area Ae is at the proximal end of the insertion section 30 and is exceedingly smaller than area Ad. The second rotational change quantities calculated based on the first rotational change quantities of areas Ad and Ae are referred to as second rotational change quantities θd and θe, respectively.

The attitude calculator 70 calculates the difference between the second rotational change quantities θd and θe to calculate the rotation quantity of the insertion section 30 with respect to the control section 40, i.e., the quantity of twist θt of the insertion section 30.

In the present modification, calculation of the quantity of twist θt enables detailed, reliable, and easy detection of the attitude change of the insertion apparatus 20. The quantity of twist θt displayed on the display 60b as shown in FIG. 11B enables the operator to easily ascertain the quantity of twist, which is the rotation quantity of the insertion section 30 with respect to the control section 40, and can improve operability.

[Fourth Modification]

Figure 12:
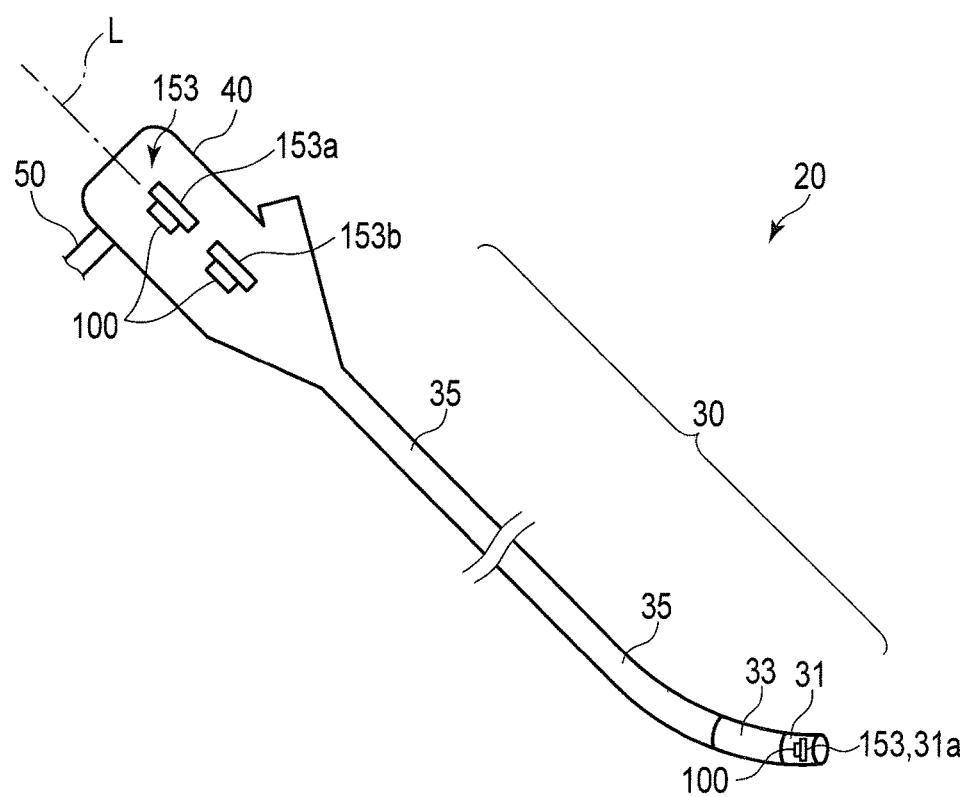
FIG. 12 is a diagram showing a fourth modification of the first embodiment, and illustrating the relationship between attitude detectors and an electronic part.

A fourth modification of the present embodiment will be described with reference to FIG. 12.

The attitude detector 100 may be integrated in advance by MEMS technology or the like with an electronic part 153 that is built in the insertion apparatus 20 and necessary for the insertion apparatus 20 to function. For example, the electronic part 153 includes at least one of an imaging device 31a built in the distal end of the insertion section 30, an electronic member 153a built in the control section 40, and a hybrid IC 153b built in the insertion apparatus 20 and integrated with an IC built in the insertion apparatus 20 on an electric substrate. The attitude detector 100 may be fixed to the inner wall of the control section 40.

In the present modification, the attitude detector 100 can be easily arranged in the insertion apparatus 20 with a limited inner space. When the attitude detector 100 is integrated with the imaging device 31a, the coordinate system of the attitude detector 100 can be aligned with the coordinate system of the imaging device 31a in advance.

Second Embodiment

Figure 13A:
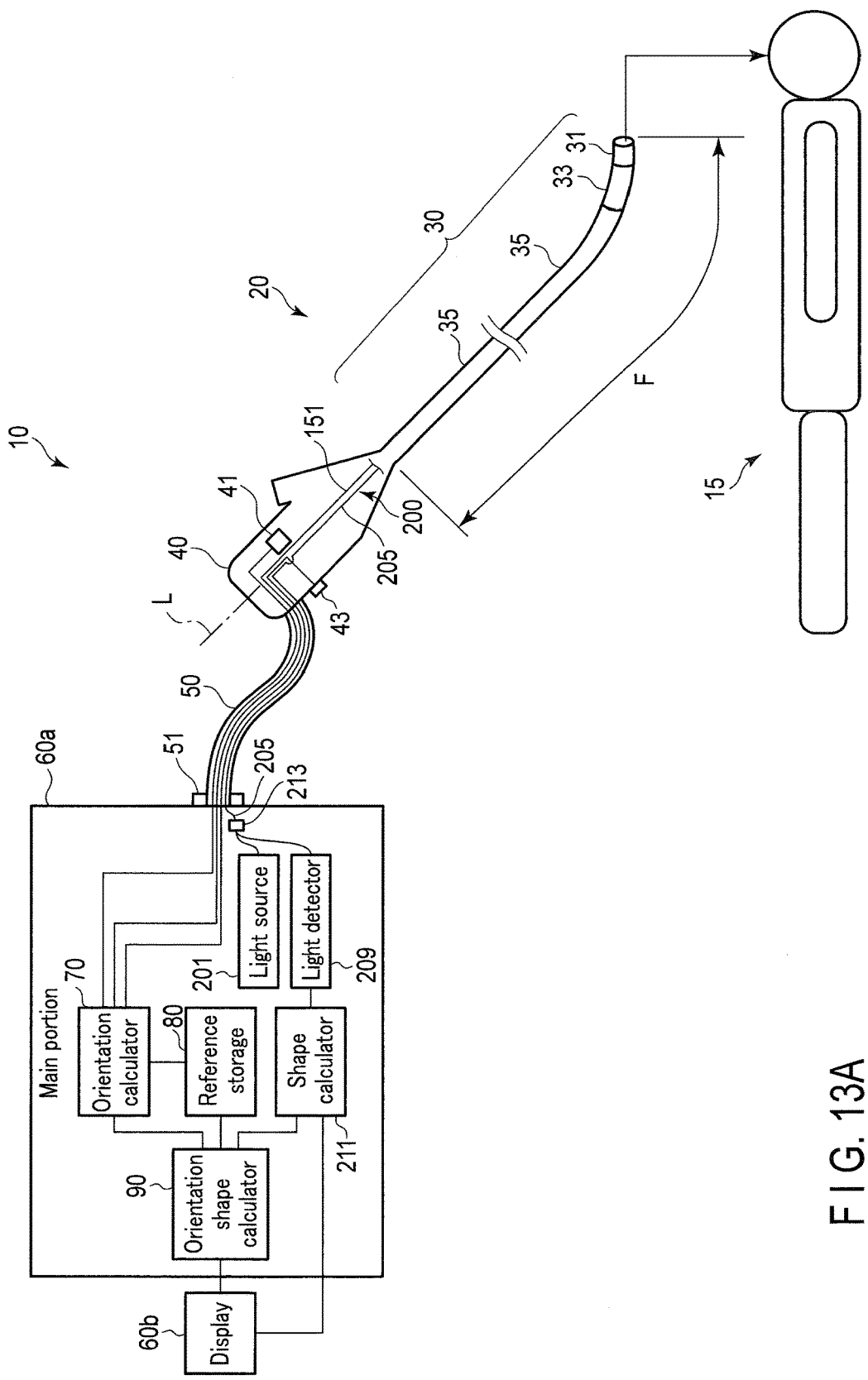
FIG. 13A is a schematic diagram of the insertion system according to a second embodiment of the present invention.

A second embodiment will be described with reference to FIGS. 13A and 13B. In this embodiment, only portions different from the first embodiment will be described.

The insertion apparatus 20 of the present embodiment is described as, but is not limited to, a flexible endoscope for medical use, for example. The insertion apparatus 20 may be, for example, a flexible endoscope for industrial use, a catheter, or a treatment tool. The insertion apparatus 20 only has to include a flexible insertion section 30.

The insertion system 10 of the present embodiment includes a fiber sensor 200 arranged in the insertion apparatus 20 and configured to detect and calculate a bend shape of a desired shape detection range (hereinafter referred to as range F). Range F of the present embodiment extends over, for example, the entire insertion section 30. Range F may extend over a part of the insertion apparatus 20 like a part of the insertion section 30 or may extend over the entire insertion apparatus 20. The bend shape includes a bend direction and a bend magnitude. For example, the fiber sensor 200 of the present embodiment is incorporated in the insertion section 30 to be bent integrally with the insertion section 30, and detects the bend shape of the insertion section 30. For example, the fiber sensor 200 is a shape sensor that detects a shape change of the insertion section 30 based on a shape change applied to the optical fiber in accordance with the shape change of the insertion section 30.

The fiber sensor 200 includes a light source 201, an optical fiber 205 provided with one or more detection targets 203 to be detected, a reflector 207, such as a mirror, a light detector 209, a shape calculator 211, and a light brancher 213. The fiber sensor 200 is a sensor that obtains the direction and magnitude of the bend of the detection target 203 by detecting the relationship between the characteristics of the incident light on the optical fiber 205 and the emitted light from the optical fiber 205.

The light source 201 is built in the main body 60a and emits light toward the optical fiber 205. The light source 201, which is another one than a light source for illumination that emits source light, emits light for detecting a bend shape. The light source 201 includes at least one of a lamp, such as a xenon lamp or a halogen lamp, and a semiconductor light source, such as an LED or an LD. The optical fiber 205 is installed in the insertion apparatus 20, extending through the connector 51 to the hard distal end 31, and guides light. The optical fiber 205 is flexible. In order to detect the bend shape of the insertion section 30 by the fiber sensor 200 detects, the detection target 203 is located in, for example, the insertion section 30. In other words, the fiber sensor 200 detects the shape of the portion where the detection target 203 is located. The reflector 207 is arranged in the distal end of the optical fiber 205. The reflector 207 reflects light guided by the optical fiber 205 back to the proximal end of the optical fiber 205.

When the insertion section 30 is bent, the optical fiber 205 is bent in accordance with the bend of the insertion section 30. In accordance with the bend, part of the light propagating through the optical fiber 205 is emitted (leaked) outside through the detection target 203. In other words, the detection target 203 is provided on a side surface of the optical fiber 205, and allows part of the propagating light to be emitted outside in accordance with the bend of the optical fiber 205. That is, the detection target 203 changes optical characteristics of the optical fiber 205, such as a light transmission quantity. When the optical fiber 205 bends in accordance with the band of the flexible insertion section 30, the light transmission quantity of the optical fiber 205 changes in accordance with the direction and magnitude of the bend. An optical signal including the information on the change in the light transmission quantity is converted into an electrical signal by the light detector 209, and is sent to the shape calculator 211. Based on the electrical signal, the shape calculator 211 calculates the bend shape, i.e., the direction and magnitude of the band, of the actually-bent portion of the insertion section 30.

The light detector 209 may include, for example, an element for spectrally dispersion, such as a spectroscope or a color filter, and a light receiving element, such as a photodiode. The shape calculator 211 may be constituted by a calculation circuit including, for example, a CPU, an ASIC, or the like.

The light source 201, the light detector 209, and the proximal end of the optical fiber 205 are optically connected to the light brancher 213. The light brancher 213 includes, for example, an optical coupler or a half mirror. The light brancher 213 guides the light emitted from the light source 201 to the optical fiber 205, and guides the return light guided by the optical fiber 205 to the light detector 209.

Here, as an example of the optical characteristics to be changed, the light transmission quantity is described; however, the optical characteristics are not limited to this, and may be a state of light, such as spectrum or polarization. In this case, the fiber sensor 200 only has to detect the state of light, such as spectrum or polarization. The detection target 203 may be formed of, for example, a substance, such as a light absorber, that reduces the intensity (quantity) of light guided by the optical fiber 205. The detection target 203 may be formed of, for example, a substance, such as a fluorescent substance, that absorbs light guided by the optical fiber 205 to emit light having a wavelength band different from that of the guided light.

When a single optical fiber 205 is provided with a single detection target 203, optical fibers 205 are installed. Alternatively, a single optical fiber 205 is provided with detection targets 203. Alternatively, a single optical fiber 205 is provided with detection targets 203, and optical fibers 205 are installed.

It is assumed that detection targets 203 are provided at different positions in the longitudinal direction of the optical fiber 205. In this case, the magnitude of the bend can be detected. Even if a single detection target 203 is provided, the magnitude of the bend can be detected.

Alternatively, it is assumed that detection targets 203 are provided at the same position or neighborhood positions in the longitudinal direction of the optical fiber 205, and different positions in the direction about the axis in the longitudinal direction. In this case, the magnitude and direction of the bend can be detected by a combination of the detection results by the detection targets 203.

The shape calculator 211 calculates the bend shape of the insertion section 30 based on the following equation (1) of the change $\Delta l$ in the light transmission quantity of the fiber sensor 200 and the bend shape $\varphi$ of the detection target 203, the equation being obtained by the measurement in advance:

$$\varphi = f(\Delta l) \qquad (1)$$

Note that the shape calculator 211 may have a conversion table storing the relationship between the change $\Delta l$ in the light transmission quantity and equation (1) and calculate the bend shape of the insertion section 30 not necessarily based on equation (1), but based on the conversion table.

The shape calculator 211 calculates the bend shape of the insertion section 30 based on the bend shape of each detection target 203 and the known length of the detection range of each detection target 203. In the calculation method, for example, the bend shape of the insertion section 30 is calculated by regarding the bend of each detection range as an arc and joining the arcs.

Since the attitude information of the insertion section 30 is unknown, provisional attitude information needs to be defined. For example, the vector (X, Y, Z) of the proximal end of the insertion section 30 is defined as (0, 0, 1), that is, the direction of the proximal end is defined as along the z axis. As bend directions of the insertion section 30, the up-down and left-right directions are predetermined. Therefore, the bend in the up-down direction is aligned with the y-axis direction, and the bend in the left-right direction is aligned with the x-axis direction. Under this condition, when the insertion section 30 is bent, in the shape calculation, the first arc from the proximal end of the insertion section 30 is calculated, the second, third, . . . , and n-th arcs are then calculated, and the adjacent arcs are joined together. In this way, the fiber sensor 200 detects the bend shape of the insertion section 30.

Since the operator cannot view the insertion section 30 inserted into the subject 15, the operator cannot ascertain the bend shape of the insertion section 30. However, the shape detected by the fiber sensor 200 is displayed on the display 60b, so that the operator can ascertain the bend shape of the insertion section 30.

However, the fiber sensor 200 cannot detect the attitude information (rotational change quantity and directional change quantity) of the insertion section 30. Therefore, the operator cannot ascertain the attitude information of the insertion section 30 from the bend shape of the insertion section 30 displayed on the display 60*b*. Even if the display 60*b* displays the bend shape of the insertion section 30 that does not reflect the attitude information, it is difficult for the operator to ascertain the attitude of the insertion section 30 inside the subject 15. For example, in order to improve operability, the operator needs to ascertain the attitude of the insertion section 30 with respect to the subject 15. Therefore, the insertion system 10 needs to detect attitude information of the insertion section 30.

To serve the need, the attitude detector 100 of the present embodiment is built in range F, i.e., the insertion section 30. Consequently, area A is included in range F, and the attitude information of the insertion section 30 calculated by the attitude calculator 70 equals the attitude information of range F. By causing area A to overlap or to be adjacent to at least a part of range F, the attitude detector 100 can detect at least one of the first rotational change quantity and first directional change quantity that are attitude information at at least one place in range F, and the attitude calculator 70 can calculate the attitude information of the insertion section 30 that is range F.

Figure 13B:
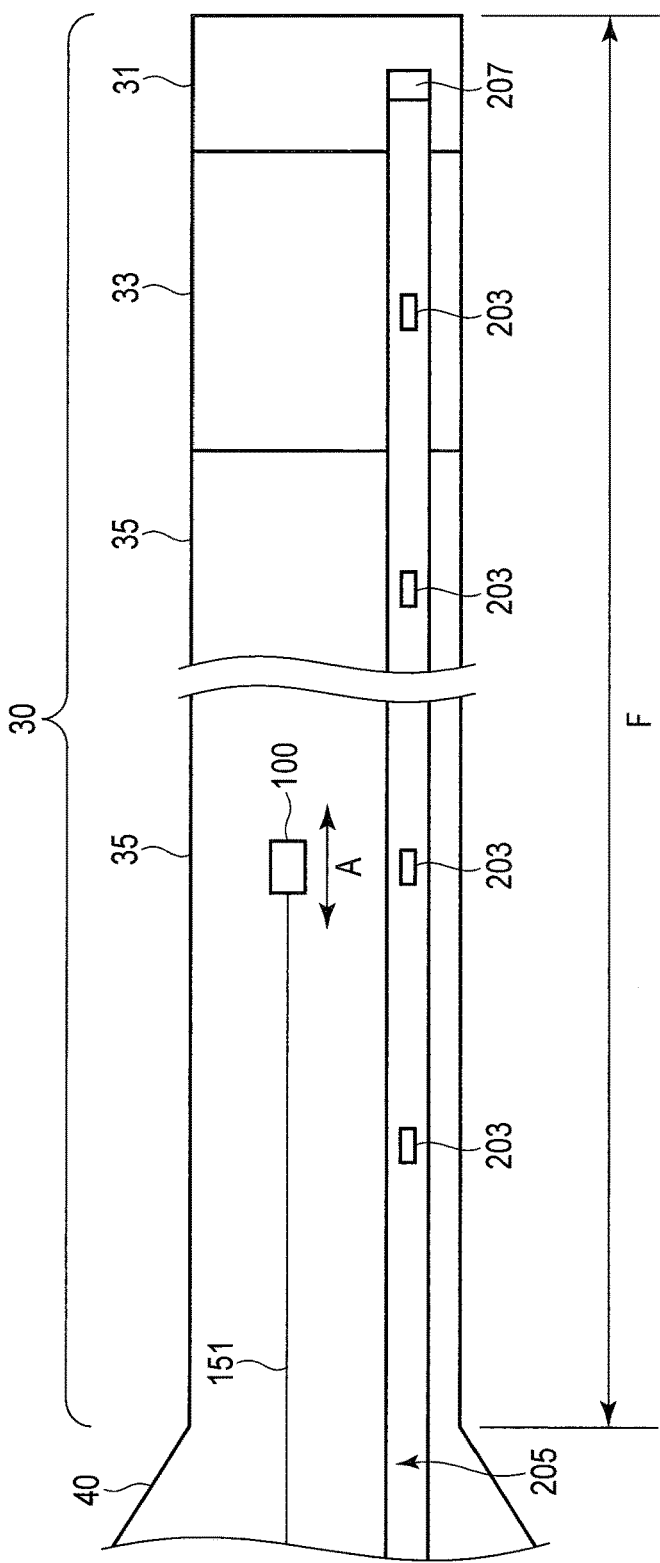
FIG. 13B is a diagram illustrating the positional relationship between an attitude detector and detection targets in the shape detection range shown in FIG. 13A.

Here, it is assumed that, unlike the configuration shown in FIG. 13B, the attitude detector 100 and area A are arranged in a portion outside range F, and the portion between area A and range F is a flexible member like the insertion section 30. In this case, the attitude of the portion between area A and range F may change. In this case, the attitude information of area A detected by the attitude detector 100 is different from the attitude information of range F, so that the attitude information of range F is not determined. Therefore, area A of the attitude detector 100 needs to overlap or be adjacent to at least a part of range F. Note that the attitude detector 100 itself is not necessarily arranged in range F, and area A only has to overlap or be adjacent to at least a part of range F. Since the configuration of the attitude detector 100 is substantially the same as that of the first embodiment, a detailed description thereof will be omitted.

The attitude calculator 70 calculates attitude information of the insertion section 30, which is range F, based on at least one of the first rotational change quantity and first directional change quantity detected by the attitude detector 100. The attitude information of range F is at least one of the second rotational change quantity that is the change quantity of range F about the axis in the longitudinal direction of range F and the second directional change quantity that is the change quantity of range F in the longitudinal direction of range F. Since the configuration of the attitude detector 100 is substantially the same as that of the first embodiment, a detailed description thereof will be omitted. The configuration of the attitude calculator 70 varies depending on the configuration of the attitude detector 100 as in the first embodiment.

The insertion system 10 includes an attitude shape calculator 90 that calculates attitude shape information of the insertion section 30 based on the attitude information of the insertion section 30 calculated by the attitude calculator 70 and the bend shape of the insertion section 30 calculated by the shape calculator 211 of the fiber sensor 200. The attitude shape calculator 90 is constituted by a calculation circuit including, for example, a CPU, an ASIC, or the like. The bend shape of the insertion section 30 calculated by the shape calculator 211 is a shape calculated based on a provisional attitude. Therefore, the attitude shape calculator 90 calculates, as attitude shape information of the insertion section 30, the bend shape of the insertion section 30 reflecting the attitude information of the insertion section 30. For example, when the second rotational change quantity included in the attitude information of the insertion section 30 is θ, the attitude shape calculator 90 performs calculation for rotating the bend shape of the insertion section 30 by θ.

Furthermore, it is assumed that the actual vector (X, Y, Z) of the insertion section 30 is detected as (X1, Y1, Z1) by the attitude detector 100. In order to define provisional attitude information, the vector (X, Y, Z) of the insertion section 30 is defined as (0, 0, 1). Therefore, the attitude shape calculator 90 performs calculation for changing the vector (X, Y, Z) of the proximal end of the insertion section 30 from (0, 0, 1) to (X1, Y1, Z1). (X, Y, Z) are coordinates of a coordinate system with respect to the room where the insertion apparatus 20 is used or the ground. In the case of the room, (X, Y, Z) are coordinates of a coordinate system with respect to a stationary object, such as a wall, a floor, or the ground.

For example, when the attitude calculator 70 calculates attitude information of the insertion section 30 with respect to the subject 15, the insertion section 30 at the time of, for example, starting insertion is aligned with the subject 15, and the reference storage 80 stores, as a reference, the attitude information of the aligned insertion section 30 when receiving a storage instruction from the instruction device 43. Then, the attitude calculator 70 calculates attitude information of the insertion section 30 with respect to the subject 15, based on the difference between the attitude information of the insertion section 30 detected later and the stored attitude information of the insertion section 30. Accordingly, the bend shape of the insertion section 30 reflecting the attitude information of the insertion section 30 with respect to the subject 15 is calculated in the present embodiment. Although the subject 15 is used as the reference; the room where the insertion apparatus 20 is used or the ground may also be used as the reference.

The attitude shape calculator 90 calculates the attitude shape information of the insertion section 30 by combining the attitude information of the insertion section 30 calculated by the attitude calculator 70 and the bend shape of the insertion section 30 calculated by the shape calculator 211. The attitude shape calculator 90 calculates a bend shape of the insertion section 30 reflecting the attitude information of the insertion section 30 in the subject 15, which is attitude shape information. Alternatively, the attitude shape calculator 90 calculates a bend shape of the insertion section 30 reflecting the attitude information of the insertion section 30 with respect to the room where the insertion section 30 is used or the ground, which is attitude shape information. Then, the display 60*b* displays the bend shape of the insertion section 30 reflecting the attitude information of the insertion section 30, which is attitude shape information.

In the present embodiment, even if the operator cannot directly view the insertion section 30 inserted into the subject 15, the operator can ascertain, through the display 60*b*, the bend shape of the insertion section 30 reflecting the attitude information of the insertion section 30 in the subject 15 or the attitude information of the insertion section 30 with respect to the room where the insertion section 30 is used or the ground. As a result, operability for the operator is improved.

In the present embodiment, although the case where the attitude detector 100 is built in the insertion section 30 is described, the configuration is not limited to this. For example, when range F extends over the entire insertion apparatus 20, the attitude detector 100 is built in the entire insertion apparatus 20 or a part of the insertion apparatus 20. The attitude detector 100 may be built in, for example, the control section 40 as will be described later. In this case, the attitude information of the insertion apparatus 20 calculated by the attitude calculator 70 equals the attitude information of range F. The attitude shape calculator 90 calculates attitude shape information of the insertion apparatus 20 based on the attitude information of the insertion apparatus 20 calculated by the attitude calculator 70 and the bend shape calculated by the fiber sensor 200. That is, the attitude shape calculator 90 calculates, as the attitude shape information of the insertion apparatus 20, the bend shape of the insertion apparatus 20 that reflects the attitude information of the insertion apparatus 20 calculated by the attitude calculator 70 and is calculated by the shape calculator 211.

It is assumed that the attitude detector 100 is built in the control section 40, as shown in FIG. 13C. In such a case, the entire control section 40, which is a rigid portion, can be regarded as area A. It is also assumed that area A is adjacent to range F. In this case, since an end of area A is continuous with (meets) an end of range F, the attitude detector 100 detects attitude information of at least a part of range F. Area A only has to overlap at least a part of range F. This overlapping includes the end of area A being continuous with the end of range F, i.e., the end of area A being adjacent to the end of range F. Although the case where the attitude detector 100 is built in a rigid control section 40 has been described, when the attitude detector 100 is built in a flexible insertion section 30, area A only has to at least partly overlap or be adjacent to range F as described above.

Here, another description on the configuration shown in FIG. 13C is provided. Since the shape of the control section 40 does not change, the shape is always known. When range F extends from the distal end side of the insertion section 30 to the proximal end of the insertion section 30, which is the boundary between the control section 40 and the insertion section 30, range F can be regarded as including the control section 40. That is, since area A overlaps a part of range F, the insertion system 10 can calculate the bend shape of the insertion section 30 reflecting the attitude information.

The inner space of the control section 40 is wider than the inner space of the insertion section 30. Therefore, the attitude detector 100 is easily incorporated. In the case where the attitude detector 100 is built in the insertion section 30, when the insertion section 30 is bent, a built-in member, such as an operation wire built in the insertion section 30, may move; due to the movement of the built-in member, the attitude detector 100 may also move. This may decrease the detection accuracy. The movement of the built-in member may also cause wear and deterioration of the attitude detector 100. Building the attitude detector 100 in the control section 40 prevents the attitude detector 100 from being influenced by the movement of the built-in member, prevents the decrease of detection accuracy, and prevents deterioration.

In the present embodiment, the attitude shape calculator 90 calculates, as the attitude shape information, the bend shape of the insertion section 30 reflecting the attitude information of the insertion section 30, but the attitude shape information is not limited to this. For example, the attitude shape calculator 90 may calculate, as the attitude shape information, the attitude at any position in range F different from the position of the attitude detector 100, or the relative position information of range F with respect to the attitude detector 100. In this case, the attitude shape calculator 90 calculates, as the attitude shape information, attitude information at a position different from the attitude information of range F based on the attitude information and the bend shape calculated by the fiber sensor 200.

[First Modification]

Hereinafter, a first modification of the present embodiment will be described with reference to FIGS. 14A, 14B, and 14C.

Figure 14A:
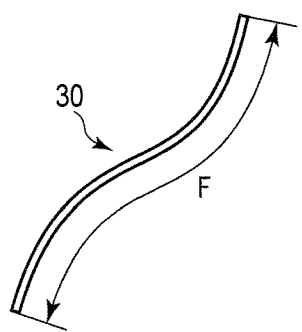
FIG. 14A is a diagram showing a first modification of the second embodiment and showing an actual bend shape reflecting actual attitude information of the entire insertion section, which is an example of the shape detection range.

FIG. 14A is a diagram showing the actual bend shape of the entire insertion section 30, which is an example of range F.

Figure 14B:
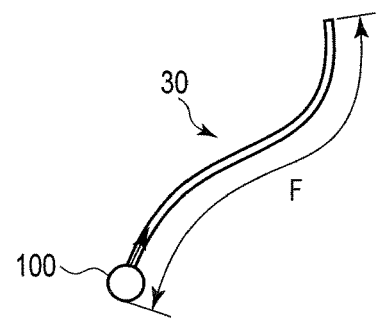
FIG. 14B is a diagram showing a bend shape of the insertion section reflecting attitude information, but involving a detection error of the fiber sensor.

FIG. 14B is a diagram showing the bend shape of the insertion section 30 reflecting the attitude information, but involving a detection error of the fiber sensor 200. In this case, after the vector of the proximal end of the insertion section 30 shown in FIG. 14A is detected by the attitude detector 100 and the bend shape of the insertion section 30 is calculated by the shape calculator 211, the attitude shape calculator 90 reflects the attitude information of the insertion section 30 in the bend shape of the insertion section 30. The error occurs, for example, due to the calculation by the shape calculator 211 based on the arcs in range F or due to a change in the light quantity in the light source 201 or the connector 51. In joining the arcs in the calculation by the shape calculator 211, the error in the direction (position) increases, by integration, from the proximal end to the distal end of the insertion section 30.

Figure 14C:
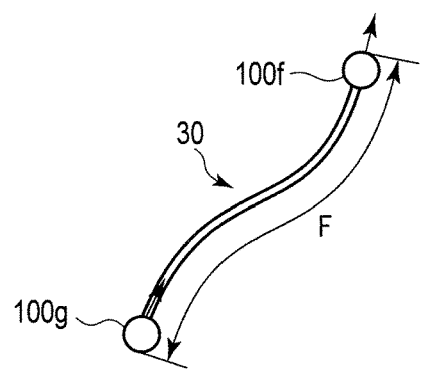
FIG. 14C is a diagram showing a bend shape of the insertion section reflecting attitude information, and involving a reduced detection error of the fiber sensor.

Therefore, as shown in FIG. 14C, the attitude detectors 100 are arranged in the distal end and proximal end of the insertion section 30 in the longitudinal direction of the insertion section 30. Hereinafter, the attitude detector 100 arranged in the distal end will be referred to as an attitude detector 100f, and the attitude detector 100 arranged in the proximal end will be referred to as an attitude detector 100g. The attitude detector 100f detects the direction of the distal end, and the attitude detector 100g detects the direction of the proximal end. The attitude detectors 100 are arranged at different positions in range F in the longitudinal direction of range F. The attitude shape calculator 90 corrects the bend shape of the insertion section 30 having an error that is calculated by the shape calculator 211, based on the detection result of the attitude detector 100, and then calculates attitude shape information.

In the present modification, for example, the attitude detectors 100 detect the directions at their respective arrangement positions.

For example, mere correction to align the direction of the proximal end of the bend shape of the insertion section 30 calculated by the shape calculator 211 with the direction of the proximal end of the insertion section 30 detected by attitude detector 100g causes an error in the direction of the distal end of the bend shape of the insertion section 30. Therefore, the attitude shape calculator 90 corrects the bend shape of the insertion section 30 having an error that is calculated by the shape calculator 211, based on each direction, and calculates the attitude shape information. For example, correction is made to align the direction of the proximal end of the bend shape of the insertion section 30 with the direction of the proximal end of the insertion section 30 detected by attitude detector 100g, and to align the direction of the distal end of the bend shape of the insertion section 30 with the direction of the distal end of the insertion section 30 detected by attitude detector 100f. As a result, the detection error is reduced.

In the present modification, two attitude detectors 100 are provided, but the number is not limited to two. Attitude detectors 100 may be arranged at different positions in range F in the longitudinal direction of range F.

[Second Modification]

Hereinafter, a second modification of the present embodiment will be described with reference to FIG. 15.

The fiber sensor 200 can detect the bend shape of the insertion section 30, which is an example of range F, but cannot detect the twist of the insertion section 30. When the insertion section 30 is twisted, an error occurs in the bend shape of the insertion section 30 calculated by the shape calculator 211.

In the present modification, attitude detectors 100 are provided. The number of attitude detectors 100 is, for example, three, and they are referred to as attitude detectors 100a, 100b, and 100c, respectively. The attitude detectors 100a, 100b, and 100c are arranged in the insertion section 30, which is range F. The attitude detectors 100a, 100b, and 100c are arranged at different positions in the insertion section 30 to detect the quantity of twist of the insertion section 30 in the longitudinal direction of the insertion section 30, and are, for example, acceleration sensors. For example, the attitude detector 100a is arranged in the proximal end of the insertion section 30, the attitude detector 100c is arranged in the distal end of the insertion section 30, and the attitude detector 100b is arranged between the attitude detectors 100a and 100c.

Areas A of the attitude detectors 100a, 100b, and 100c are referred to as area Aa, Ab, and Ac, respectively. Areas Aa, Ab, and Ac are minute areas. The second rotational change quantities calculated based on the first rotational change quantities of areas Aa, Ab, and Ac are referred to as second rotational change quantities θa, θb, and θc, respectively. As in FIGS. 3A and 3B, the second rotational change quantities θa, θb, and θc each indicate the angle formed by the negative-side axis of the y axis and the direction g of gravity separated into components on the X-Y plane.

The attitude calculator 70 calculates a twist of the insertion section 30 based on the second rotational change quantities θa, θb, and θc. Specifically, the attitude calculator 70 calculates the quantity of twist of the insertion section 30 based on the difference between the second rotational change quantities θa and θb, and the difference between the second rotational change quantities θb and θc. As described above, the attitude calculator 70 calculates the quantity of twist in the insertion section 30 based on the difference between the second rotational change quantities calculated based on the first rotational change quantities detected by adjacent attitude detectors 100.

The attitude shape calculator 90 corrects the bend shape of the insertion section 30 having an error that is calculated by the shape calculator 211 based on the quantity of twist, and then calculates attitude shape information. The error of the bend shape is thereby reduced.

In the present modification, three attitude detectors 100 are provided, but the number is not limited to three. Attitude detectors 100 only have to be arranged at different positions in range F in the longitudinal direction of range F.

[Third Modification]

A third modification of the present embodiment will be described with reference to FIGS. 13B and 16.

In the present embodiment, for example, when the attitude calculator 70 calculates attitude information of the insertion apparatus 20 with respect to the subject 15, the insertion apparatus 20 at the time of, for example, starting insertion is aligned with the subject 15, and the reference storage 80 stores, as a reference, the attitude information of the aligned insertion apparatus 20 when receiving a storage instruction from the instruction device 43. Based on the difference between the attitude information of the insertion apparatus 20 detected later and the stored attitude information of the insertion apparatus 20, the attitude calculator 70 calculates attitude information of the insertion apparatus 20 with respect to the subject 15.

However, when the insertion system 10 is used, a patient, who is the subject 15, needs to move or to be moved for the circumstances of the operator or the use of the insertion apparatus 20. That is, the attitude information of the subject 15 may change.

For that reason, the insertion system 10 includes at least one subject attitude detector (hereinafter referred to as attitude detectors 17) for the subject 15, which function similarly to the attitude detector 100. Here, one attitude detector 17 is provided, but attitude detectors 17 may be provided at different positions. The attitude detector 17 is arranged on or around a predetermined part of the subject 15, into which the insertion apparatus 20 is inserted. This part is, for example, the abdomen of the patient. A belt (not shown) is attached to the attitude detector 17, and the belt is worn on the patient so that the attitude detector 17 is attached to the part. The attitude detector 17 has an attitude detection area (hereinafter referred to as area B) desirably defined. The attitude detector 17 is configured to detect at least one of the first rotation change quantity that is the change quantity of area B about the axis in the longitudinal direction of area B, and the first direction change quantity that is the change quantity of area B in the longitudinal direction of area B. The first rotational change quantity and the first directional change quantity are included in attitude information of area B, i.e., the subject 15. The attitude detector 17 is electrically connected to the attitude calculator 70 through a signal line. The attitude detector 17 may be electrically connected to the attitude calculator 70 wirelessly. The attitude detector 17 always outputs the detection result in real time to the attitude calculator 70.

Since the configuration of the attitude detector 17 is the same as that of the attitude detector 100, a detailed description thereof will be omitted. Since correction of the first rotational change quantity and the first directional change quantity is the same as in the first embodiment, a detailed description thereof will be omitted.

The attitude calculator 70 calculates attitude information of the subject 15 based on at least one of the first rotational change quantity and first directional change quantity detected by the attitude detector 17. Since the calculation by the attitude calculator 70 is the same as that in the first embodiment, a detailed description thereof will be omitted.

Based on the attitude information of the subject 15 and the attitude information of the insertion apparatus 20, the attitude calculator 70 calculates attitude information of the insertion apparatus 20 relative to the subject 15 with reference to attitude information of the subject 15.

The attitude shape calculator 90 calculates attitude shape information based on the attitude information of the insertion apparatus 20 calculated by the attitude calculator 70, the attitude information of the subject 15 calculated by the attitude calculator 70, and the bend shape of the insertion section 30 calculated by the shape calculator 211. The attitude shape information is a bend shape of the insertion apparatus 20 reflecting attitude information of the insertion apparatus 20 relative to the subject 15.

As described above, according to the present embodiment, even if the attitude information of the subject 15 changes, the operator can ascertain, through the display 60b, the bend shape of the insertion section 30 reflecting the attitude information of the insertion apparatus 20 relative to the subject 15. As a result, operability for the operator is improved.

The present invention is not limited to the above embodiments as they are, and can be embodied by modifying structural elements in the implementation stage without departing from the gist thereof. Furthermore, various inventions can be formed by appropriately combining structural elements disclosed in the above embodiments.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An insertion system comprising:
an insertion apparatus including an insertion section to be inserted into a subject;
a fiber sensor arranged in the insertion section and configured to detect a bend shape of a desired shape detection range of the insertion section;
at least one attitude sensor arranged in the insertion apparatus and configured to detect at least one of a first rotational change quantity related to a change quantity of rotation about an axis in a longitudinal direction of the insertion apparatus at an arrangement position, and a first directional change quantity related to a change quantity of a direction of the longitudinal direction of the insertion apparatus at the arrangement position; and
a processor including hardware, the processor being configured to:
calculate attitude information of the insertion apparatus including a change quantity of rotation of the bend shape about an axis in the longitudinal direction of the insertion apparatus and a change quantity of a longitudinal direction of the insertion apparatus, based on at least one of the first rotational change quantity and the first directional change quantity detected by the attitude sensor; and
calculate attitude shape information, based on the bend shape detected by the fiber sensor and the calculated attitude information.

2. The insertion system according to claim 1, further comprising a memory configured to store a correction value for correcting an axis displacement of the attitude sensor with respect to the insertion apparatus that occurs when the attitude sensor is built in the insertion apparatus,
wherein the processor is further configured to correct, based on the correction value, at least one of the first rotational change quantity and first directional change quantity detected by the attitude sensor.

3. The insertion system according to claim 2, wherein the processor calculates the attitude information of the insertion apparatus based on at least one of the corrected first rotational change quantity and corrected first directional change quantity corrected.

4. The insertion system according to claim 3, wherein the attitude sensor includes a gravity sensor configured to detect a direction of gravity acting on a desirably-defined attitude detection area of the attitude sensor and then detect the first rotational change quantity based on the detected direction of gravity.

5. The insertion system according to claim 4, wherein the processor is configured to:
extract gravity information from the first rotational change quantity corrected by the correction unit after being detected by the gravity sensor; and
calculate, based on the extracted gravity information, a second rotational change quantity that is a change quantity of the insertion apparatus about the axis in the longitudinal direction of the insertion apparatus and included in the attitude information of the insertion apparatus.

6. The insertion system according to claim 5, further comprising a reference memory configured to, when receiving a storage instruction, receive the calculated second rotational change quantity and then store the second rotational change quantity as a reference,
wherein the processor calculates a current second rotational change quantity with reference to the second rotational change quantity stored in the reference memory.

7. The insertion system according to claim 4, wherein the gravity sensor includes an acceleration sensor configured to detect the direction of gravity by two more axes and then detect the first rotational change quantity based on the detected direction of gravity.

8. The insertion system according to claim 4, wherein the gravity sensor includes:
a weight movable in accordance with the direction of gravity that changes in accordance with rotation of the insertion apparatus and acts on the attitude sensor; and
detection surfaces allowing detecting a position or direction of the weight with respect to the insertion apparatus and then detecting the first rotational change quantity based on the detected position or direction.

9. The insertion system according to claim 3, wherein the attitude sensor includes a gyro sensor configured to detect at least one of the first rotational change quantity and first directional change quantity in an angular velocity of a desirably-defined attitude detection area of the attitude sensor.

10. The insertion system according to claim 9, wherein the gyro sensor detects a first orthogonal rotational change quantity about a direction orthogonal to a longitudinal direction of the attitude detection area, the first orthogonal rotational change quantity being the detected angular velocity, and
wherein the processor is configured to perform at least one of calculation of a second rotational change quantity that is a change quantity of the insertion apparatus about the axis in the longitudinal direction of the insertion apparatus included in the attitude information of the insertion apparatus, based on the corrected first rotational change quantity after being detected by the gyro sensor, and calculation of a second orthogonal rotational change quantity that is a change quantity of the insertion apparatus about a direction orthogonal to the longitudinal direction of the insertion apparatus included in the attitude information of the insertion apparatus, based on the corrected first orthogonal rotation change quantity after being detected by the gyro sensor.

11. The insertion system according to claim 10, wherein the processor is configured to calculate, based on the calculated second orthogonal rotational change quantity, a second directional change quantity that is a change quantity of the insertion apparatus in the longitudinal direction of the insertion apparatus included in the attitude information of the insertion apparatus.

12. The insertion system according to claim 11, further comprising a reference memory configured to, when receiving a storage instruction, receive the calculated second rotational change quantity and then store the second rotational change quantity as a reference,
wherein the processor calculates a current second rotational change quantity with reference to the second rotational change quantity stored in the reference memory.

13. The insertion system according to claim 11, further comprising a reference memory configured to, when receiving a storage instruction, receive the calculated second directional change quantity and then store the second directional change quantity as a reference,
wherein the processor calculates a current second directional change quantity with reference to the second directional change quantity stored in the reference memory.

14. The insertion system according to claim 3, wherein the attitude sensor includes:
a gravity sensor configured to detect a direction of gravity acting on a desirably-defined attitude detection area of the attitude sensor and then detect at least one of the first rotational change quantity and a first orthogonal rotational change quantity in the detected direction of gravity; and
a gyro sensor configured to detect at least one of the first rotational change quantity and the first orthogonal rotational change quantity in an angular velocity of the attitude detection area, and
wherein the processor compensates a second rotational change quantity or a second orthogonal rotational change quantity, calculated based on the first rotational change quantity or first orthogonal change quantity detected by the gravity sensor, with a second rotational change quantity or a second orthogonal rotational change quantity calculated based on the first rotational change quantity or first orthogonal rotational change quantity detected by the gyro sensor, the second rotational change quantity being a change quantity of the insertion apparatus about the axis in the longitudinal direction of the insertion apparatus included in the attitude information of the insertion apparatus, and the second orthogonal rotational change quantity being a change quantity of the insertion apparatus about a direction orthogonal to the longitudinal direction of the insertion apparatus included in the attitude information of the insertion apparatus.

15. The insertion system according to claim 14, wherein the gyro sensor detects the first orthogonal rotational change quantity about a direction orthogonal to a longitudinal direction of the attitude detection area, the first orthogonal rotational change quantity being the detected angular velocity, and
wherein the processor is configured to:
extract gravity information from the corrected first rotational change quantity after being detected by the gravity sensor; and
perform at least one of calculation of a second rotational change quantity that is a change quantity of the insertion apparatus about the axis in the longitudinal direction of the insertion apparatus included in the attitude information of the insertion apparatus, based on the corrected first rotational change quantity after being detected by the gyro sensor, and calculation of a second orthogonal rotational change quantity that is a change quantity of the insertion apparatus about a direction orthogonal to the longitudinal direction of the insertion apparatus included in the attitude information of the insertion apparatus, based on the corrected first orthogonal rotation change quantity after being detected by the gyro sensor.

16. The insertion system according to claim 15, wherein the processor is configured to calculate, based on the calculated second orthogonal rotational change quantity, a second directional change quantity that is a change quantity of the insertion apparatus in the longitudinal direction of the insertion apparatus included in the attitude information of the insertion apparatus.

17. The insertion system according to claim 16, further comprising a reference memory configured to, when receiving a storage instruction, receive the calculated second rotational change quantity and then store the second rotational change quantity as a reference,
wherein the processor calculates a current second rotational change quantity with reference to the second rotational change quantity stored in the reference memory.

18. The insertion system according to claim 16, further comprising a reference memory configured to, when receiving a storage instruction, receive the calculated second directional change quantity and then store the second directional change quantity as a reference,
wherein the processor calculates a current second directional change quantity with reference to the second directional change quantity stored in the reference memory.

19. The insertion system according to claim 3, wherein the attitude sensor includes a terrestrial magnetism sensor configured to detect a direction of a terrestrial magnetism and then detect the first directional change quantity based on the detected direction of the terrestrial magnetism.

20. The insertion system according to claim 19, wherein the processor is configured to calculate, based on the corrected first direction change quantity after being detected by the terrestrial magnetism sensor, a second directional change quantity that is a change quantity of the insertion apparatus in the longitudinal direction of the insertion apparatus included in the attitude information of the insertion apparatus.

21. The insertion system according to claim 20, further comprising a reference memory configured to, when receiving a storage instruction, receive the calculated second directional change quantity, and then store the second directional change quantity as a reference,
wherein the processor calculates a current second directional change quantity with reference to the second directional change quantity stored in the reference memory.

22. The insertion system according to claim 3, wherein the at least one attitude sensor comprises a plurality of attitude sensors, and the processor calculates the attitude information of the insertion apparatus based on at least one of the first rotational change quantity and first directional change quantity detected by each of the attitude sensors.

23. The insertion system according to claim 22, wherein the attitude sensors are arranged at different positions in the insertion apparatus in the longitudinal direction of the insertion apparatus, and
wherein the processor calculates a quantity of twist based on a difference between the attitude information of the insertion apparatus calculated based on the first rotational change quantities detected by adjacent attitude sensors of the attitude sensors.

24. The insertion system according to claim 1, wherein a desirably-defined attitude detection area of the attitude sensor overlaps or is adjacent to at least a part of the shape detection range, and
wherein the calculated attitude information of the insertion apparatus includes attitude information of the shape detection range.

25. The insertion system according to claim 24, wherein the processor calculates the bend shape reflecting the attitude information of the insertion apparatus as the attitude shape information.

26. The insertion system according to claim 24, wherein the processor calculates relative position information of the shape detection range with respect to the attitude sensor as the attitude shape information.

27. The insertion system according to claim 24, wherein the processor calculates, based on the attitude information and the bend shape calculated by the fiber sensor, attitude information at a position different from the attitude information of the shape detection range as the attitude shape information.

28. The insertion system according to claim 24, wherein the at least one attitude sensor comprises a plurality of attitude sensors,
wherein the attitude sensors are arranged at different positions in the longitudinal direction of the shape detection range, and
wherein the processor corrects the bend shape of the shape detection range calculated by the fiber sensor based on detection results of the attitude sensors detectors and then calculates the attitude shape information.

29. The insertion system according to claim 28, wherein the attitude sensors detect directions at respective arrangement positions, and
wherein the processor corrects the bend shape of the shape detection range calculated by the fiber sensor based on the directions and then calculates the attitude shape information.

30. The insertion system according to claim 28, wherein the processor calculates a quantity of twist in the shape detection range based on a difference between the attitude information of the insertion apparatus calculated based on the first rotational change quantities detected by adjacent attitude sensors of the attitude sensors, and
wherein the processor corrects the bend shape of the shape detection range calculated by the fiber sensor based on the quantity of twist and then calculates the attitude shape information.

31. The insertion system according to claim 24, wherein the processor calculates the attitude information of the insertion apparatus relative to the subject with reference to attitude information of the subject.

32. The insertion system according to claim 31, further comprising at least one subject attitude sensor having a desirably-defined subject attitude detection area, arranged on the subject, and configured to detect at least one of a first subject rotational change quantity that is a change quantity of the subject attitude detection area about an axis in a longitudinal direction of the subject attitude detection area and a first subject directional change quantity that is a change quantity of the subject attitude detection area in the longitudinal direction of the subject attitude detection area,
wherein the processor:
calculates the attitude information of the subject based on at least one of the first subject rotational change quantity and first subject directional change quantity detected by the subject attitude detector, and
calculates the attitude shape information based on the calculated attitude information of the insertion apparatus, the attitude information of the subject calculated by the attitude calculator, and the bend shape of the shape detection area calculated by the fiber sensor.

33. The insertion system according to claim 1, wherein the attitude sensor is integrated with an electronic part that is built in the insertion apparatus and is necessary for the insertion apparatus to function.

34. The insertion system according to claim 33, wherein the electronic part includes at least one of an imaging device built in a distal end of the insertion section, an electronic member built in the control section of the insertion apparatus, and a hybrid IC built in the insertion apparatus.

* * * * *